United States Patent
Maimon et al.

(10) Patent No.: US 10,039,637 B2
(45) Date of Patent: Aug. 7, 2018

(54) HEART VALVE DOCKING DEVICES AND IMPLANTING METHODS

(71) Applicant: Edwards Lifesciences Corporation, Irvine, CA (US)

(72) Inventors: David Maimon, Haifa (IL); Hernan Altman, Kiryat Tivon (IL)

(73) Assignee: Edwards Lifesciences Corporation, Irvine, CA (US)

( * ) Notice: Subject to any disclaimer, the term of this patent is extended or adjusted under 35 U.S.C. 154(b) by 154 days.

(21) Appl. No.: 15/040,772

(22) Filed: Feb. 10, 2016

(65) Prior Publication Data
US 2016/0228247 A1 Aug. 11, 2016

Related U.S. Application Data

(60) Provisional application No. 62/115,010, filed on Feb. 11, 2015.

(51) Int. Cl.
*A61F 2/24* (2006.01)

(52) U.S. Cl.
CPC .......... *A61F 2/2409* (2013.01); *A61F 2/2412* (2013.01); *A61F 2/2433* (2013.01); *A61F 2230/0067* (2013.01); *A61F 2230/0091* (2013.01); *A61F 2250/006* (2013.01)

(58) Field of Classification Search
CPC ........ A61F 2/24; A61F 2/2409; A61F 2/2427; A61F 2/243; A61F 2/2433; A61F 2230/0091; Y10S 623/90
USPC ................................. 606/151; 623/2.1, 2.11
See application file for complete search history.

(56) References Cited

U.S. PATENT DOCUMENTS

| | | | |
|---|---|---|---|
| 3,755,823 | A | 9/1973 | Hancock |
| 4,035,849 | A | 7/1977 | Angell et al. |
| 4,490,859 | A | 1/1985 | Black et al. |
| 4,512,338 | A | 4/1985 | Balko et al. |
| 4,777,951 | A | 10/1988 | Cribier et al. |
| 4,787,899 | A | 11/1988 | Lazarus |

(Continued)

FOREIGN PATENT DOCUMENTS

| | | |
|---|---|---|
| CN | 1684644 A | 10/2005 |
| CN | 1714766 A | 1/2006 |

(Continued)

OTHER PUBLICATIONS

Bonhoeffer et at., "Percutaneous Replacement of Pulmonary valve in a Right-Ventricle to Pulmonary-Artery Prosthetic Conduit with Valve Dysfunction," Early Report, The Lancet, vol. 356, Oct. 21, 2000.

(Continued)

*Primary Examiner* — Melanie Tyson
(74) *Attorney, Agent, or Firm* — Thomas C. Richardson

(57) ABSTRACT

A device is in various embodiments configured to repair a native heart valve or to secure a prosthetic heart valve within a native valve of the heart of a patient. Embodiments of the device include at least an upper coil and a lower coil, where the device is configured to assume an axially expanded state where the entire upper coil is positioned on a first side of the lower coil relative to the central axis, and an axially compressed state where at least a portion of the upper coil is positioned on a second side of at least a portion of the lower coil opposite to the first side relative to the central axis.

17 Claims, 26 Drawing Sheets

(56) References Cited

U.S. PATENT DOCUMENTS

| | | | |
|---|---|---|---|
| 4,796,629 A | 1/1989 | Grayzel |
| 4,856,516 A | 8/1989 | Hillstead |
| 4,878,495 A | 11/1989 | Grayzel |
| 4,966,604 A | 10/1990 | Reiss |
| 4,994,077 A | 2/1991 | Dobben |
| 5,059,177 A | 10/1991 | Towne et al. |
| 5,192,297 A | 3/1993 | Hull |
| 5,282,847 A | 2/1994 | Trescony et al. |
| 5,370,685 A | 12/1994 | Stevens |
| 5,403,305 A | 4/1995 | Sauter et al. |
| 5,411,552 A | 5/1995 | Andersen et al. |
| 5,443,500 A | 8/1995 | Sigwart |
| 5,545,214 A | 8/1996 | Stevens |
| 5,558,644 A | 9/1996 | Boyd et al. |
| 5,584,803 A | 12/1996 | Stevens et al. |
| 5,591,195 A | 1/1997 | Taheri et al. |
| 5,607,464 A | 3/1997 | Trescony et al. |
| 5,665,115 A | 9/1997 | Cragg |
| 5,769,812 A | 6/1998 | Stevens et al. |
| 5,800,508 A | 9/1998 | Goicoechea et al. |
| 5,855,597 A | 1/1999 | Jayaraman |
| 5,925,063 A | 7/1999 | Khosravi |
| 5,957,949 A | 9/1999 | Leonhardt et al. |
| 6,027,525 A | 2/2000 | Suh et al. |
| 6,120,534 A | 9/2000 | Ruiz |
| 6,168,614 B1 | 1/2001 | Andersen et al. |
| 6,221,091 B1 | 4/2001 | Khosravi |
| 6,235,042 B1 | 5/2001 | Katzman |
| 6,245,102 B1 | 6/2001 | Jayaraman |
| 6,302,906 B1 | 10/2001 | Goicoechea et al. |
| 6,306,141 B1 | 10/2001 | Jervis |
| 6,406,492 B1 | 6/2002 | Lytle |
| 6,409,758 B2 | 6/2002 | Stobie et al. |
| 6,419,696 B1 * | 7/2002 | Ortiz .................... A61F 2/2409 623/2.37 |
| 6,425,916 B1 | 7/2002 | Garrison et al. |
| 6,432,134 B1 | 8/2002 | Anson et al. |
| 6,454,799 B1 | 9/2002 | Schreck |
| 6,458,153 B1 | 10/2002 | Bailey et al. |
| 6,461,382 B1 | 10/2002 | Cao |
| 6,482,228 B1 | 11/2002 | Norred |
| 6,527,979 B2 | 3/2003 | Constantz |
| 6,582,462 B1 | 6/2003 | Andersen et al. |
| 6,652,578 B2 | 11/2003 | Bailey et al. |
| 6,730,118 B2 | 5/2004 | Spenser et al. |
| 6,730,121 B2 | 5/2004 | Ortiz et al. |
| 6,733,525 B2 | 5/2004 | Yang et al. |
| 6,767,362 B2 | 7/2004 | Schreck |
| 6,797,002 B2 | 9/2004 | Spence et al. |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 6,964,684 B2 | 11/2005 | Ortiz et al. |
| 7,018,406 B2 | 3/2006 | Seguin et al. |
| 7,018,408 B2 | 3/2006 | Bailey et al. |
| 7,037,334 B1 | 5/2006 | Hlavka et al. |
| 7,077,861 B2 | 7/2006 | Spence |
| 7,101,395 B2 | 9/2006 | Tremulis et al. |
| 7,125,421 B2 | 10/2006 | Tremulis et al. |
| 7,166,126 B2 | 1/2007 | Spence et al. |
| 7,166,127 B2 | 1/2007 | Spence et al. |
| 7,276,078 B2 | 10/2007 | Spenser et al. |
| 7,276,084 B2 | 10/2007 | Yang et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,404,824 B1 | 7/2008 | Webler et al. |
| 7,431,726 B2 | 10/2008 | Spence et al. |
| 7,462,191 B2 | 12/2008 | Spenser et al. |
| 7,510,575 B2 | 3/2009 | Spenser et al. |
| 7,585,321 B2 | 9/2009 | Cribier |
| 7,618,446 B2 | 11/2009 | Andersen et al. |
| 7,655,034 B2 | 2/2010 | Mitchell et al. |
| 7,737,060 B2 | 6/2010 | Strickler et al. |
| 7,780,726 B2 | 8/2010 | Seguin |
| 7,785,366 B2 | 8/2010 | Maurer et al. |
| 7,951,195 B2 | 5/2011 | Antonsson et al. |
| 7,959,672 B2 | 6/2011 | Salahieh et al. |
| 7,993,394 B2 | 8/2011 | Hariton et al. |
| 8,029,556 B2 | 10/2011 | Rowe |
| 8,128,691 B2 | 3/2012 | Keranen |
| 8,167,932 B2 | 5/2012 | Bourang et al. |
| 8,323,335 B2 | 12/2012 | Rowe et al. |
| 8,377,115 B2 | 2/2013 | Thompson |
| 8,398,708 B2 | 3/2013 | Meiri et al. |
| 8,449,605 B2 | 5/2013 | Lichtenstein et al. |
| 8,449,606 B2 | 5/2013 | Eliasen et al. |
| 8,652,203 B2 | 2/2014 | Quadri et al. |
| 8,657,872 B2 | 2/2014 | Seguin |
| 8,663,322 B2 | 3/2014 | Keranen |
| 8,672,998 B2 | 3/2014 | Lichtenstein et al. |
| 8,734,507 B2 | 5/2014 | Keranen |
| 8,795,352 B2 | 8/2014 | O'Beirne et al. |
| 8,986,373 B2 | 3/2015 | Chau et al. |
| 9,078,747 B2 | 7/2015 | Conklin |
| 9,095,434 B2 | 8/2015 | Rowe |
| 9,119,718 B2 | 9/2015 | Keranen |
| 9,237,886 B2 | 1/2016 | Seguin et al. |
| 9,364,326 B2 | 6/2016 | Yaron |
| 9,463,268 B2 | 10/2016 | Spence |
| 9,474,599 B2 | 10/2016 | Keranen |
| 9,622,863 B2 | 4/2017 | Karapetian et al. |
| 2002/0026094 A1 | 2/2002 | Roth |
| 2002/0032481 A1 | 3/2002 | Gabbay |
| 2002/0045936 A1 | 4/2002 | Moe |
| 2002/0138135 A1 | 9/2002 | Duerig et al. |
| 2002/0173841 A1 | 11/2002 | Ortiz et al. |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0167089 A1 | 9/2003 | Lane |
| 2003/0212454 A1 | 11/2003 | Scott et al. |
| 2003/0225420 A1 | 12/2003 | Wardle |
| 2004/0138745 A1 | 7/2004 | Macoviak et al. |
| 2004/0167620 A1 | 8/2004 | Ortiz et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0096736 A1 | 5/2005 | Osse et al. |
| 2005/0119735 A1 | 6/2005 | Spence et al. |
| 2005/0137691 A1 | 6/2005 | Salahieh et al. |
| 2005/0182486 A1 | 8/2005 | Gabbay |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2006/0025857 A1 | 2/2006 | Bergheim et al. |
| 2006/0058872 A1 | 3/2006 | Salahieh et al. |
| 2006/0149350 A1 | 7/2006 | Patel et al. |
| 2006/0265056 A1 | 11/2006 | Nguyen et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0112422 A1 | 5/2007 | Dehdashtian |
| 2007/0185572 A1 | 8/2007 | Solem et al. |
| 2007/0203503 A1 | 8/2007 | Salahieh et al. |
| 2007/0203575 A1 | 8/2007 | Forster et al. |
| 2007/0213813 A1 | 9/2007 | Von Segesser et al. |
| 2007/0265700 A1 | 11/2007 | Eliasen et al. |
| 2008/0033542 A1 | 2/2008 | Antonsson et al. |
| 2008/0114442 A1 | 5/2008 | Mitchell et al. |
| 2008/0125853 A1 | 5/2008 | Bailey et al. |
| 2008/0208330 A1 | 8/2008 | Keranen |
| 2008/0228265 A1 | 9/2008 | Spence et al. |
| 2008/0275503 A1 | 11/2008 | Spence et al. |
| 2009/0157175 A1 | 6/2009 | Benichou |
| 2009/0177278 A1 | 7/2009 | Spence |
| 2009/0259307 A1 | 10/2009 | Gross et al. |
| 2009/0276040 A1 | 11/2009 | Rowe et al. |
| 2009/0281619 A1 | 11/2009 | Le et al. |
| 2009/0319037 A1 | 12/2009 | Rowe et al. |
| 2010/0049313 A1 | 2/2010 | Alon et al. |
| 2010/0076549 A1 | 3/2010 | Keidar et al. |
| 2010/0145440 A1 | 6/2010 | Keranen |

(56) References Cited

U.S. PATENT DOCUMENTS

| | | | |
|---|---|---|---|
| 2010/0152839 A1 | 6/2010 | Shandas et al. | |
| 2010/0161047 A1 | 6/2010 | Cabiri | |
| 2010/0168844 A1 | 7/2010 | Toomes et al. | |
| 2010/0198347 A1 | 8/2010 | Zakay et al. | |
| 2010/0312333 A1 | 12/2010 | Navia et al. | |
| 2010/0318184 A1 | 12/2010 | Spence | |
| 2011/0015729 A1 | 1/2011 | Jimenez et al. | |
| 2011/0098802 A1 | 4/2011 | Braido et al. | |
| 2011/0106247 A1 | 5/2011 | Miller et al. | |
| 2011/0218621 A1 | 9/2011 | Antonsson et al. | |
| 2011/0224785 A1 | 9/2011 | Hacohen | |
| 2011/0245911 A1 | 10/2011 | Quill et al. | |
| 2011/0319990 A1 | 12/2011 | Macoviak et al. | |
| 2012/0016464 A1 | 1/2012 | Seguin | |
| 2012/0053680 A1 | 3/2012 | Bolling et al. | |
| 2012/0059458 A1 | 3/2012 | Buchbinder et al. | |
| 2012/0123529 A1 | 5/2012 | Levi et al. | |
| 2012/0150287 A1 | 6/2012 | Forster et al. | |
| 2012/0215236 A1* | 8/2012 | Matsunaga | A61B 17/0644 606/151 |
| 2012/0259409 A1 | 10/2012 | Nguyen et al. | |
| 2012/0283820 A1 | 11/2012 | Tseng et al. | |
| 2012/0310328 A1 | 12/2012 | Olson et al. | |
| 2012/0316643 A1 | 12/2012 | Keranen | |
| 2013/0006352 A1 | 1/2013 | Yaron | |
| 2013/0023985 A1 | 1/2013 | Khairkhahan et al. | |
| 2013/0190857 A1 | 7/2013 | Mitra et al. | |
| 2013/0274873 A1 | 10/2013 | Delaloye et al. | |
| 2013/0304197 A1 | 11/2013 | Buchbinder et al. | |
| 2013/0310917 A1 | 11/2013 | Richter et al. | |
| 2013/0310928 A1 | 11/2013 | Morriss et al. | |
| 2013/0317598 A1 | 11/2013 | Rowe et al. | |
| 2013/0331929 A1 | 12/2013 | Mitra et al. | |
| 2014/0074299 A1 | 3/2014 | Endou et al. | |
| 2014/0172070 A1 | 6/2014 | Seguin | |
| 2014/0194981 A1 | 7/2014 | Menk et al. | |
| 2014/0200661 A1 | 7/2014 | Pintor et al. | |
| 2014/0236287 A1 | 8/2014 | Clague et al. | |
| 2014/0277417 A1 | 9/2014 | Schraut et al. | |
| 2014/0277419 A1 | 9/2014 | Garde et al. | |
| 2014/0277424 A1 | 9/2014 | Oslund | |
| 2014/0330372 A1 | 11/2014 | Weston et al. | |
| 2014/0343671 A1 | 11/2014 | Yohanan et al. | |
| 2014/0350667 A1 | 11/2014 | Braido et al. | |
| 2014/0379074 A1* | 12/2014 | Spence | A61F 2/2418 623/2.11 |
| 2015/0073545 A1 | 3/2015 | Braido | |
| 2015/0073546 A1 | 3/2015 | Braido | |
| 2015/0230921 A1 | 8/2015 | Chau et al. | |
| 2015/0282931 A1 | 10/2015 | Brunnett et al. | |
| 2015/0335428 A1 | 11/2015 | Keranen | |
| 2015/0374493 A1 | 12/2015 | Yaron et al. | |
| 2016/0074165 A1 | 3/2016 | Spence et al. | |
| 2016/0095705 A1 | 4/2016 | Keranen et al. | |
| 2016/0184095 A1 | 6/2016 | Spence et al. | |
| 2016/0199177 A1 | 7/2016 | Spence et al. | |
| 2016/0256276 A1 | 9/2016 | Yaron | |
| 2017/0007399 A1 | 1/2017 | Keranen | |
| 2017/0007402 A1 | 1/2017 | Zerkowski et al. | |
| 2017/0217385 A1 | 8/2017 | Rinkleff et al. | |

FOREIGN PATENT DOCUMENTS

| | | |
|---|---|---|
| CN | 101588771 A | 11/2009 |
| DE | 19532846 A1 | 3/1997 |
| DE | 19546692 A1 | 6/1997 |
| DE | 19857887 A1 | 7/2000 |
| DE | 19907646 A1 | 8/2000 |
| EP | 0103546 A1 | 3/1984 |
| EP | 0592410 A1 | 4/1994 |
| EP | 0597967 A1 | 5/1994 |
| EP | 0850607 A1 | 7/1998 |
| EP | 1432369 A1 | 6/2004 |
| EP | 1521550 A2 | 4/2005 |
| EP | 1796597 A2 | 6/2007 |
| EP | 1827314 A1 | 9/2007 |
| EP | 1296618 B1 | 1/2008 |
| EP | 2072027 A1 | 6/2009 |
| EP | 1827314 B1 | 12/2010 |
| EP | 2620125 A1 | 7/2013 |
| EP | 2726018 A2 | 5/2014 |
| EP | 2806829 A2 | 12/2014 |
| EP | 3269330 A1 | 1/2018 |
| FR | 2788217 A1 | 7/2000 |
| FR | 2815844 A1 | 5/2002 |
| SU | 1271508 A1 | 11/1986 |
| WO | 9117720 A1 | 11/1991 |
| WO | 1991017720 A1 | 11/1991 |
| WO | 9301768 A1 | 2/1993 |
| WO | 9829057 A1 | 7/1998 |
| WO | 9940964 A1 | 8/1999 |
| WO | 9947075 A1 | 9/1999 |
| WO | 0041652 A1 | 7/2000 |
| WO | 0047139 A1 | 8/2000 |
| WO | 0149213 A2 | 7/2001 |
| WO | 0154625 A1 | 8/2001 |
| WO | 0162189 A1 | 8/2001 |
| WO | 0164137 A1 | 9/2001 |
| WO | 0176510 A2 | 10/2001 |
| WO | 0222054 A1 | 3/2002 |
| WO | 0236048 A1 | 5/2002 |
| WO | 0247575 A2 | 6/2002 |
| WO | 03047468 A1 | 6/2003 |
| WO | 05/034812 | 4/2005 |
| WO | 2005084595 A1 | 9/2005 |
| WO | 05/102015 | 11/2005 |
| WO | 2005102015 A2 | 11/2005 |
| WO | 2006011127 A2 | 2/2006 |
| WO | 06/111391 | 10/2006 |
| WO | 06/138173 | 12/2006 |
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008015257 A2 | 2/2008 |
| WO | 2008091515 A2 | 7/2008 |
| WO | 2009033469 A1 | 3/2009 |
| WO | 2010121076 A2 | 10/2010 |
| WO | 2013110722 A2 | 8/2013 |
| WO | 2013114214 A2 | 8/2013 |
| WO | 2015023579 A1 | 2/2015 |
| WO | 2015023862 A2 | 2/2015 |
| WO | 2015127264 A1 | 8/2015 |
| WO | 2015198125 A1 | 12/2015 |
| WO | 2016038017 A1 | 3/2016 |
| WO | 2016040881 A1 | 3/2016 |
| WO | 2016130820 A1 | 8/2016 |

OTHER PUBLICATIONS

Casselman et al., "Reducing Operative Morality in Valvular Reoperations: The "valve in ring" Procedure," Brief Technique Reports, The Journal of Thoracic and Cardiovascular Surgery, vol. 141, No. 5. May 2011.

Cheung et al, Live Case Transmissions, NYHA III CHF, Case Summary, Sep. 23, 2010, St. Paul's Hospital/University of British Columbia.

Cheung et al,"Transapical Transcatheter Mitral Valve-in-Valve Implantation in a Human," The Society of Thoracic Surgeons, 2009.

Descoutures et al., "Transcatheter Valve-in-Ring Implantation After Failure of Surgical Mitral Repair," European Journal of Cardio-Thoracic Surgery 44, e8-e15, 2013.

Himbert et al., "Transseptal Implantation of a Transcatheter Heart Valve in a Mitral Annuloplasty Ring to Treat Mitral Repair Failure," Circulation Cardiovascular Interventions, American Heart Association, 2011.

Himbert, Dominique, "Transvenous Mitral Valve Repair Replacement After Failure of Surgical Ring Annuloplasty," Research Correspondence, Journal of the American College of Cardiology, 2012.

Kempfert et al., "Minimally invasive off-pump valve-in-a-ring implantation: the atrial transcatheter approach for re-operative

(56) References Cited

OTHER PUBLICATIONS mitral valve replacement after failed repair," European Journal of Cardiothoracic Surgery, 2009, 35:965-969.

Ma et al., "Double-Crowned Valved Stents for Off-Pump Mitral Valve Replacement," European Journal of Cardio-Thoracic Surgery, 28, 194-199, 2005.

Shuto et al., "Percutaneous Transvenous Melody Valve-in-Ring Procedure for Mitral Valve Replacement," J AM Coll Cardiol, 58(24): 2475-2480, 2011.

Walther et al., "Human Minimally Invasive Off-Pump Valve-in-a-Valve Implantation," Case Reports, The Society of Thoracic Surgeons, 2008.

Walther et al., "Valve-in-a-Valve Concept for Transcatheter Minimally Invasive Repeat Xenograph Implantation," Preclinical Studies, Journal of the American College of Cardiology, 2007.

Webb et al., "Mitral Valve in Valve," TCT Sep. 2009, Live Case: 30 Minutes, St. Paul's Hospital/University of British Columbia.

Webb et al., "Transcatheter Valve-in-Valve Implantation for Failed Bioprosthetic Heart Valves," Journal of the American Heart Association, 11, Apr. 27, 2010.

Weger et al., "First-in-Man Implantation of a Trans-Catheter Aortic Valve in a Mitral Annuloplasty Ring: Novel Treatment Modality for Failed Mitral Valve Repair," European Journal of Cardio-Thoracic Surgery 39, 1054-1056, 2011.

Wenaweser et al., "Percutaneous Aortic Valve Replacement for Severe Aortic Regurgitation in Degenerated Bioprosthesis: The First Valve Procedure Using Corevalve Revalving System," Catheterization and Cardiovascular Interventions, 70:760-764, 2007.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Bailey, Percutaneous Expandable Prosthetic Valves, Testbook of Interventional Cardiology, Chapter 75.

H.R. Andersen "History of Percutaneous Aortic Valve Prosthesis," Herz No. 34. pp. 343-346. 2009.

Andersen, H.R., et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.

D. Pavcnik: Development and Initial Experimental Evaluation of a Prosthetic Aortic Valve for Transcatheter Placement; Cardiovascular Radiology (1992) 183, pp. 151-154.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

\* cited by examiner

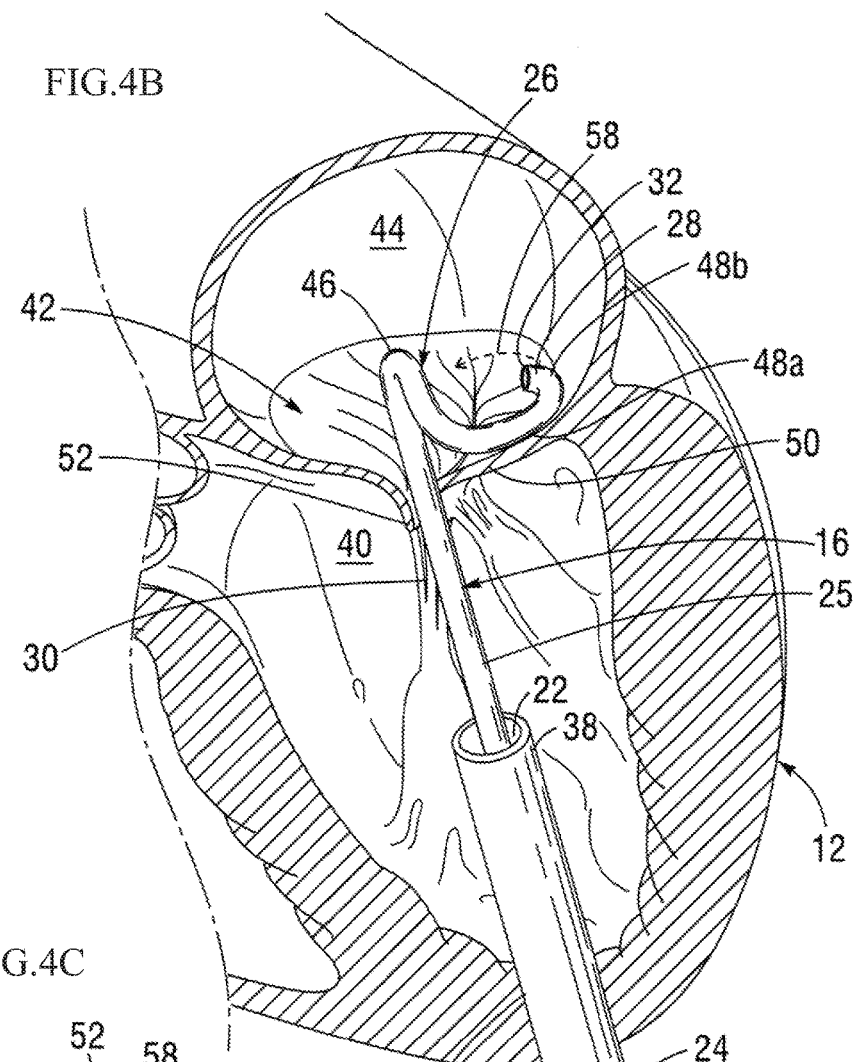
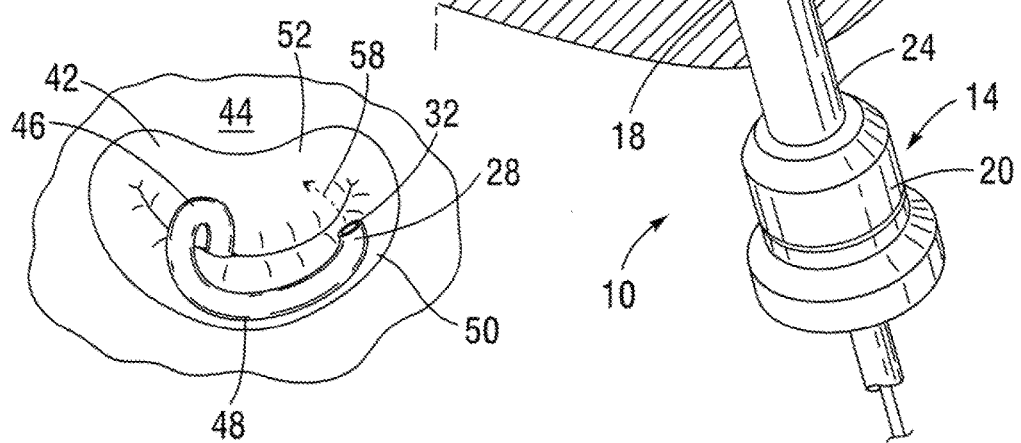

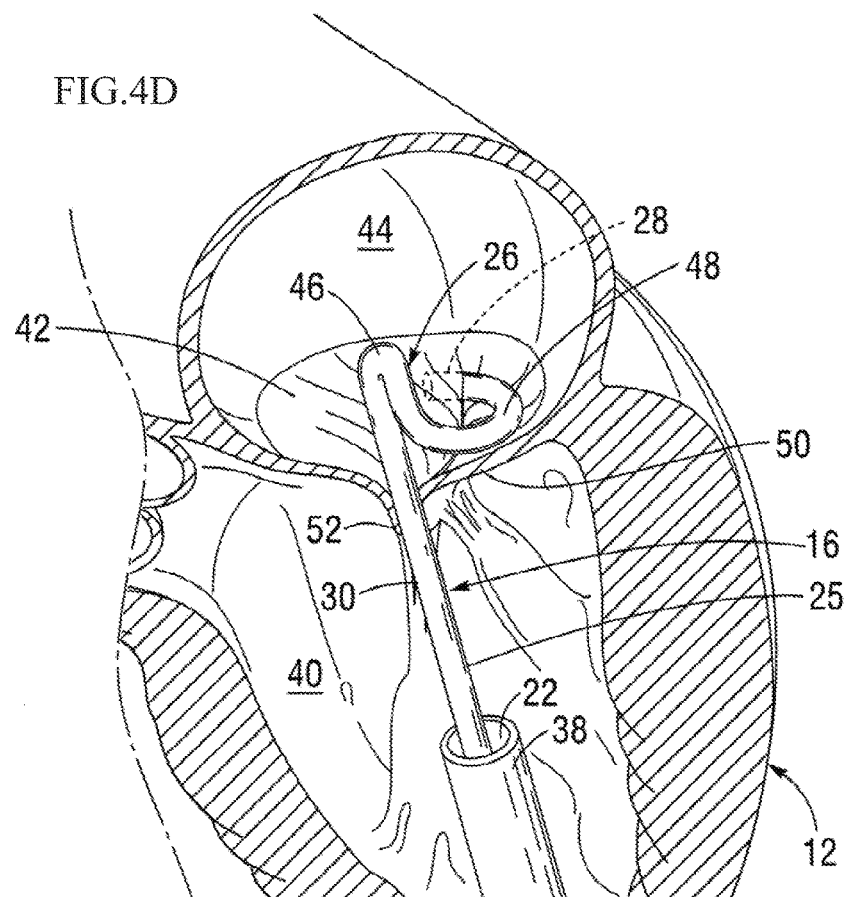
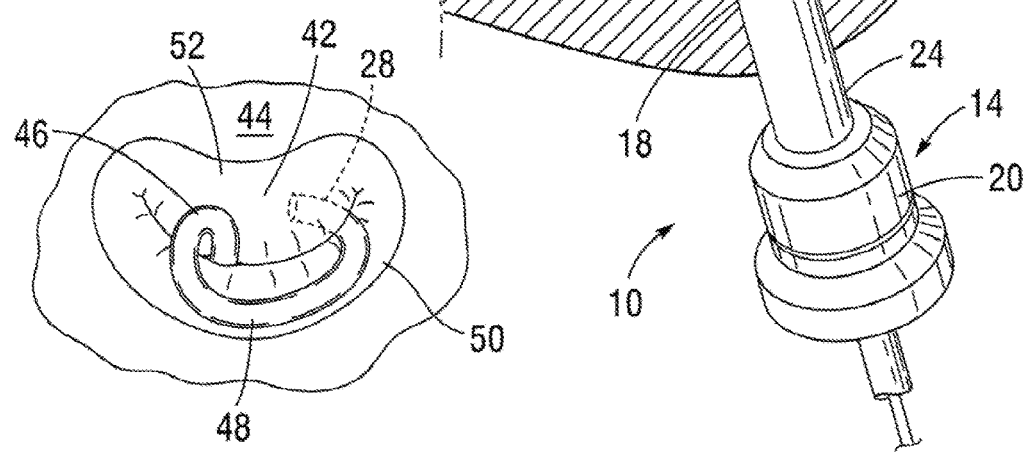
FIG.4D
FIG.4E

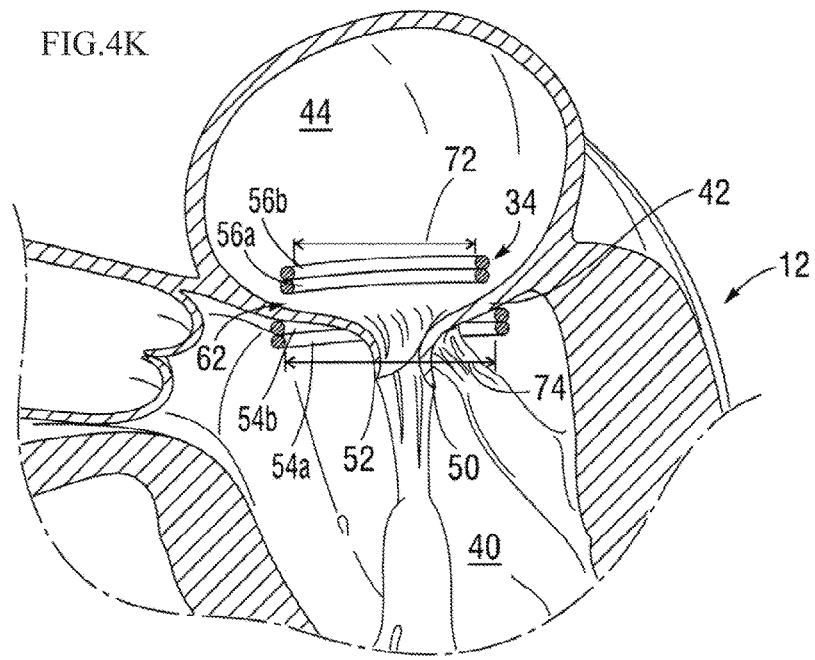
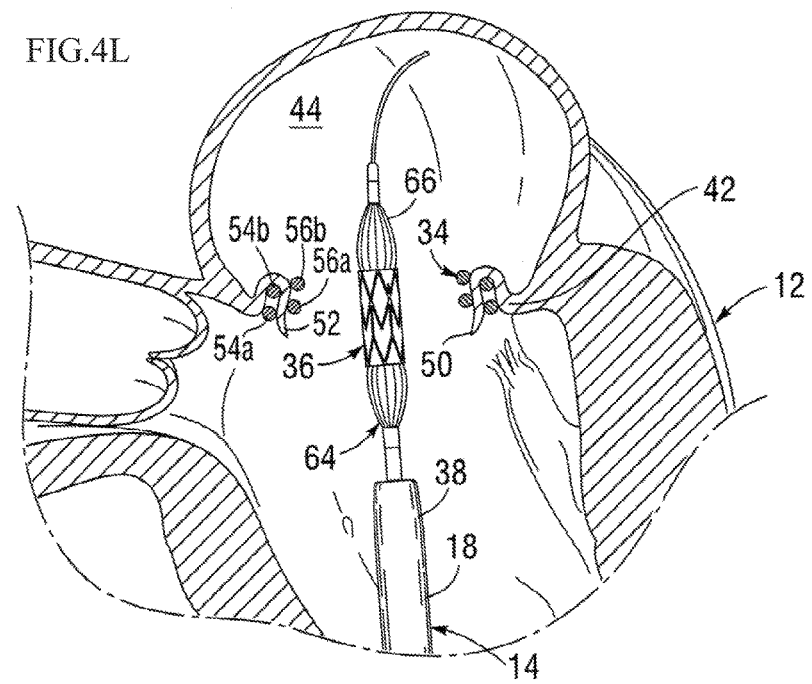

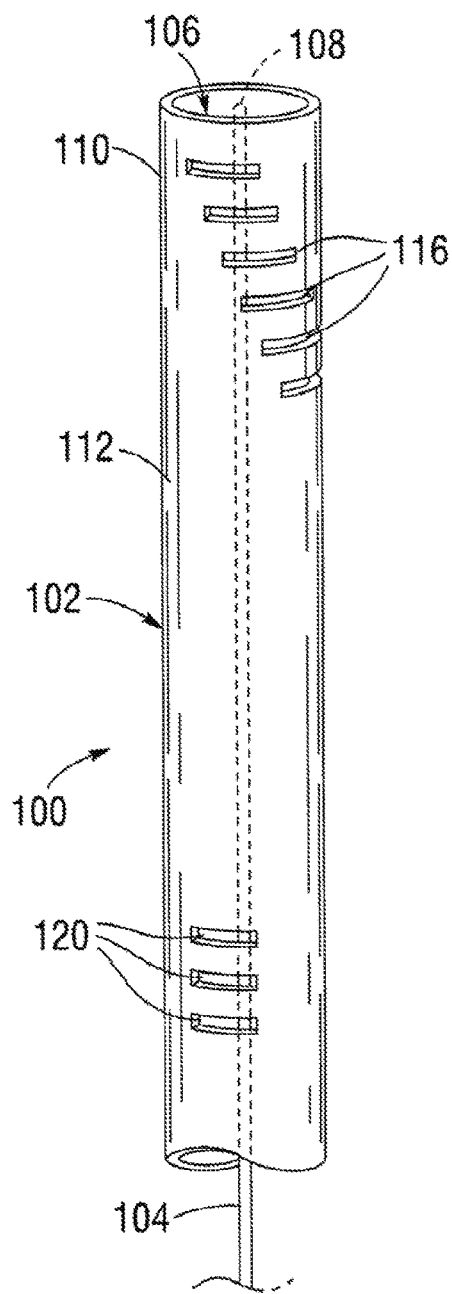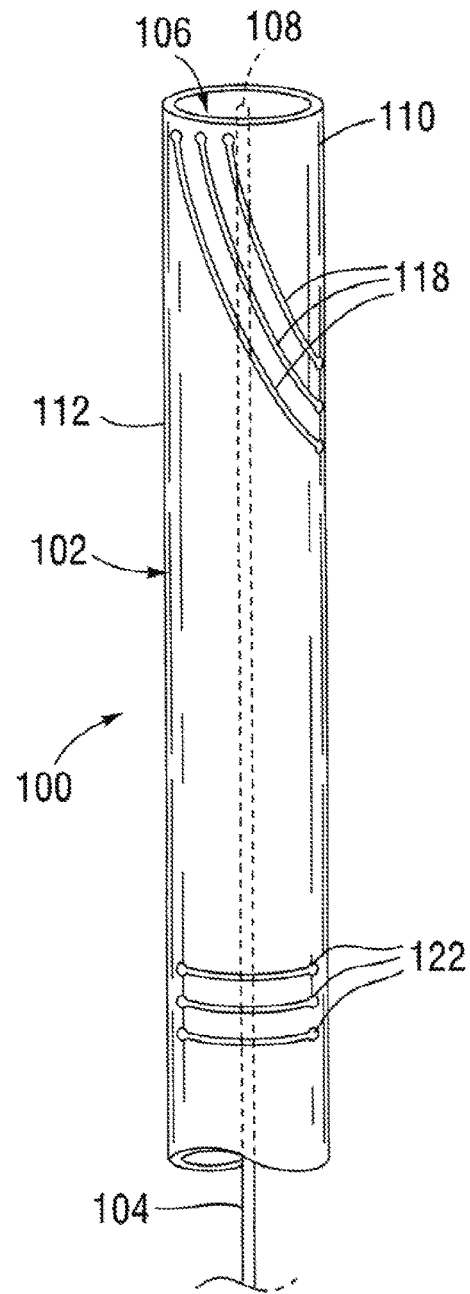

HEART VALVE DOCKING DEVICES AND IMPLANTING METHODS

CROSS-REFERENCE TO RELATED APPLICATION

This application claims priority to and the benefit of U.S. Provisional Patent Application Ser. No. 62/115,010, filed Feb. 11, 2015, the contents of which are hereby incorporated by reference in their entirety.

BACKGROUND

Field

The present disclosure generally concerns prosthetic heart valves and associated devices and related methods for implanting such devices. More specifically, the disclosure relates to the repair and replacement of heart valves that have malformations and/or dysfunctions, where an additional dock or anchor is utilized together with the prosthetic heart valve at the implant site, and methods of implanting such anchors and/or prosthetic heart valves.

Description of Related Art

Referring generally to FIGS. 1A-1B, the native mitral valve controls the flow of blood from the left atrium to the left ventricle of the human heart. The mitral valve has a very different anatomy than other native heart valves. The mitral valve includes an annulus made up of native valve tissue surrounding the mitral valve orifice, and a pair of cusps or leaflets extending downward from the annulus into the left ventricle. The mitral valve annulus can form a "D" shaped, oval shaped, or otherwise non-circular cross-sectional shape having major and minor axes. An anterior leaflet can be larger than a posterior leaflet of the valve, forming a generally "C" shaped boundary between the abutting free edges of the leaflets when they are closed together.

When operating properly, the anterior leaflet and the posterior leaflet of the mitral valve function together as a one-way valve to allow blood to flow only from the left atrium to the left ventricle. After the left atrium receives oxygenated blood from the pulmonary veins, the muscles of the left atrium contract and the left ventricle dilates (also referred to as "ventricular diastole" or "diastole"), and the oxygenated blood that is collected in the left atrium flows into the left ventricle. Then, the muscles of the left atrium relax and the muscles of the left ventricle contract (also referred to as "ventricular systole" or "systole"), to move the oxygenated blood out of the left ventricle and through the aortic valve to the rest of the body. The increased blood pressure in the left ventricle during ventricular systole urges the two leaflets of the mitral valve together, thereby closing the one-way mitral valve so that blood cannot flow back into the left atrium. To prevent the two leaflets from prolapsing under the pressure and folding back through the mitral annulus toward the left atrium during ventricular systole, a plurality of fibrous cords called chordae tendineae tether the leaflets to papillary muscles in the left ventricle.

One common form of valvular heart disease is mitral valve leak, also known as mitral regurgitation. Mitral regurgitation occurs when the native mitral valve fails to close properly and blood flows back into the left atrium from the left ventricle during the systolic phase of heart contraction. Mitral regurgitation has different causes, such as leaflet prolapse, dysfunctional papillary muscles, and/or stretching of the mitral valve annulus resulting from dilation of the left ventricle. In addition to mitral regurgitation, mitral narrowing or stenosis is another example of valvular heart disease.

Like the mitral valve, the aortic valve is susceptible to complications such as aortic valve stenosis. One method for treating such valvular heart disease includes the use of a prosthetic valve implanted within the native heart valve. These prosthetic valves can be implanted using a variety of techniques, including various transcatheter techniques. One transcatheter technique that is commonly used for accessing a native valve is the transseptal technique, where a catheter accesses the left side of the heart via a femoral vein, the inferior vena cava, the right atrium, and then a puncture hole in the interatrial septum. A prosthetic valve can then be mounted in a crimped state on the end portion of a second, flexible and/or steerable catheter, advanced to the implantation site, and then expanded to its functional size, for example, by inflating a balloon on which the valve is mounted. Alternatively, a self-expanding prosthetic valve can be retained in a radially compressed state within a sheath of a delivery catheter, and the prosthetic valve can be deployed from the sheath, which allows the prosthetic valve to expand to its functional state.

Another common transcatheter technique for implanting a prosthetic valve is a transventricular approach, where a small incision is made in the chest wall and the ventricular wall of a patient, and then a catheter or introducer sheath is inserted into the left ventricle. A delivery catheter containing or holding the prosthetic valve can then be advanced through the introducer sheath to the implantation site.

Such prosthetic valves are generally better developed for implantation or use at the aortic valve. However, similar catheter-based prosthetic valves can be more difficult to apply or implant at the native mitral valve due to the structural differences between the aortic and mitral valves. For example, the mitral valve has a more complex subvalvular apparatus, which includes the chordae tendineae. Additionally, the native mitral valve is less circular in shape and typically does not provide sufficient structure for anchoring and resisting migration of a prosthetic valve.

SUMMARY

Since many valves have already been developed for the aortic position, it would be desirable to try to take advantage of these existing valve technologies and to utilize the same or similar valves for tricuspid, pulmonic and mitral valve replacements. One way of utilizing these preexisting prosthetic valves is to use the prosthetic valves together with an anchor or other docking station that will form a more appropriately shaped implant site at the native valve annulus, so that the prosthetic valve can be implanted more securely, while reducing or eliminating leakage around the valve after implantation. For example, a mitral anchor or docking station can form a more circular bore at the annulus to more closely match the circular profiles of existing aortic valve implants. In this manner, an existing valve implant developed for the aortic position, perhaps with some modification, could then be implanted at the mitral position together with such an anchor. In addition, such anchors could also potentially be used at the heart's other native valves to more securely anchor prosthetic valves at those sites as well.

Described herein are embodiments of prosthetic devices that are primarily intended to be implanted at one of the native mitral, aortic, tricuspid, or pulmonary valve regions of a human heart, as well as apparatuses and methods for implanting the same. The prosthetic devices can be used to repair the native valve annulus, as well as to position and secure a prosthetic heart valve in the native valve region.

The disclosed devices can include a helical anchor having a plurality of turns or coils, where the helical anchor can assume an axially collapsed position where portions of at least two of the coils align or overlap in a radial direction.

In one embodiment, a helical device for implanting at a native heart valve of a heart of a patient includes an upper coil and a lower coil, and a central axis extending through the upper coil and the lower coil. The device is configured to assume an axially expanded state where the entire upper coil is positioned on a first side of the lower coil relative to the central axis, and is also configured to assume an axially compressed state where at least a portion of the upper coil is positioned on a second side of at least a portion of the lower coil opposite to the first side relative to the central axis. The device can include a first set of one or more coils comprising the upper coil having a first inner diameter, and a second set of one or more coils comprising the lower coil having an inner diameter different from the first inner diameter.

In certain embodiments, the device can include a first set of coils having at least two coils and a second set of coils having at least two coils. At least one of the coils of the first set of coils is positioned relative to the central axis between two coils of the second set of coils when the device is in the compressed state. The first set of coils can be configured to be positioned on a ventricular side of a native valve, and the second set of coils can be configured to be positioned on an atrial side of the native valve. Preferably, the upper and lower coils are made from a shape-memory material, such a Nitinol.

In another embodiment, a method of implanting a helical device, including an upper coil and a lower coil, at a native valve of a heart of a patient, involves positioning the lower coil on a ventricular side of the native valve, positioning the upper coil on an atrial side of the native valve, such that the entire upper coil is positioned on a first side of the lower coil relative to a central axis of the device, and adjusting the device to a position where at least a portion of the upper coil is positioned on a second side of at least a portion of the lower coil opposite to the first side relative to the central axis.

The method can include implanting a prosthetic heart valve within the device. The prosthetic heart valve is positioned in the device when the prosthetic heart valve is in a radially compressed state, and the prosthetic heart valve is radially expanded such that a radial pressure is applied between the prosthetic heart valve and the device to anchor the prosthetic heart valve within the device In another embodiment, a system for securing a prosthetic heart valve at a native heart valve of a heart of a patient includes a helical docking device including an upper coil and a lower coil, where a central axis extends through the upper coil and the lower coil, and a prosthetic heart valve configured to be held in the docking device. The docking device is configured to assume an axially expanded state where the entire upper coil is positioned on a first side of the lower coil relative to the central axis, and is also configured to assume an axially compressed state where at least a portion of the upper coil is positioned on a second side of at least a portion of the lower coil opposite to the first side relative to the central axis. The system can include a delivery catheter configured to deploy the docking device at the native heart valve.

BRIEF DESCRIPTION OF THE DRAWINGS

The foregoing and other objects, features, and advantages of the invention will become more apparent from the following detailed description using the accompanying figures. In the drawings:

FIGS. 4A-4M show one embodiment of a delivery apparatus and method for implanting a helical docking device and a prosthetic valve at the native mitral valve of a heart, using a transventricular technique;

FIGS. 9A-9C show perspective views of a portion of a delivery catheter for a helical docking device, according to one embodiment.

DETAILED DESCRIPTION

Figure 1A:
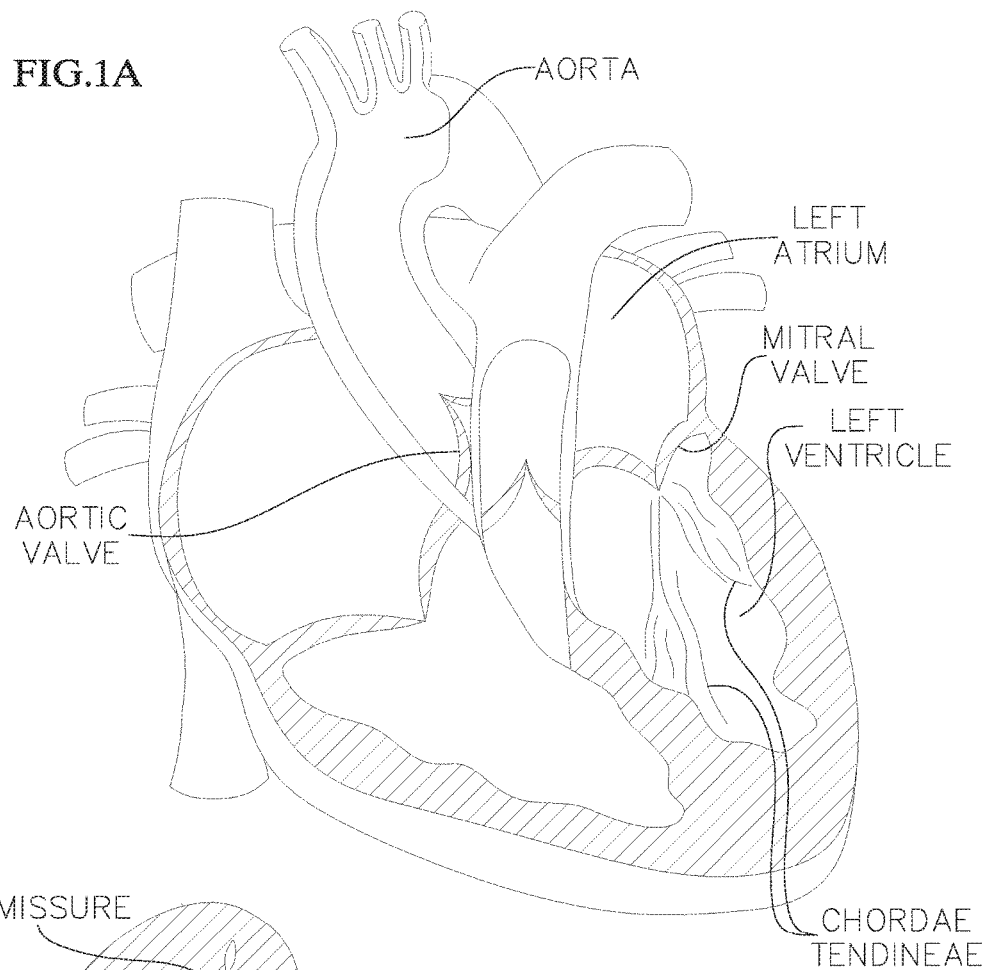
FIG. 1A shows a schematic cross-sectional view of a human heart.
Figure 1B:
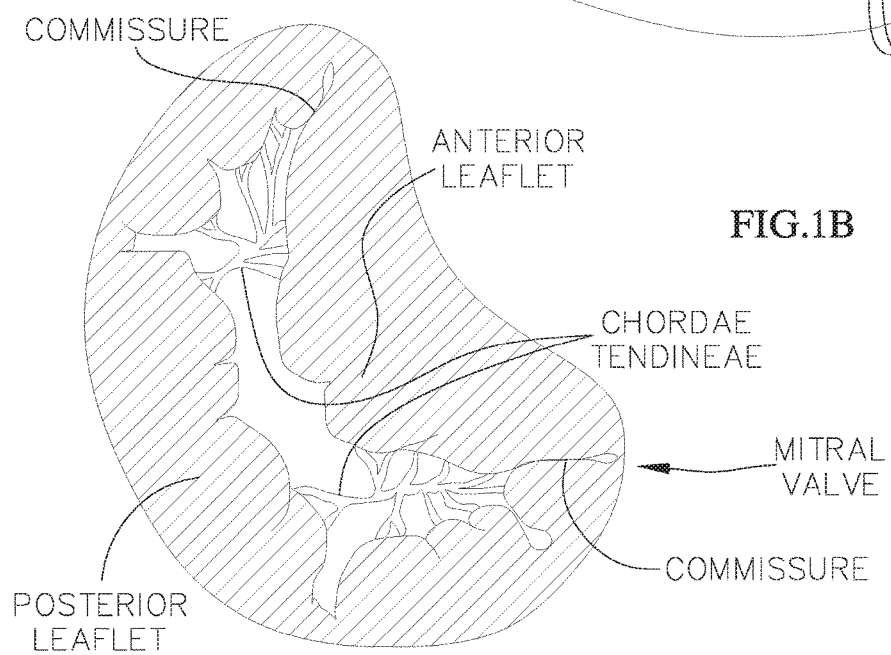
FIG. 1B shows a schematic top view of the mitral valve annulus of a heart.

Described herein are embodiments of prosthetic devices that are primarily intended to be implanted at one of the native mitral, aortic, tricuspid, or pulmonary valve regions of a human heart, as well as apparatuses and methods for implanting the same. The prosthetic devices can be used to repair a native valve and to position and secure a prosthetic heart valve in the native valve region. These prosthetic devices can improve the functionality of the prosthetic heart valves, in order to better repair replace or replicate the functionality of a defective native heart valve. The present disclosure is directed toward all features and aspects of the various disclosed embodiments, both alone and in various combinations and sub-combinations with one another.

In particular embodiments, a prosthetic assembly includes an anchoring or docking device configured to be implanted at or adjacent the native valve and configured to receive and retain a prosthetic valve. The docking device can be delivered and implanted in a minimally invasive manner via the left ventricle and/or the left atrium, after which a separate prosthetic valve can be delivered and implanted within the docking device in a minimally invasive manner.

In particular embodiments, a docking device includes a helical anchor having a plurality of turns or coils with at least one of the coils having a negative pitch relative to an adjacent coil when the helical anchor is in at least one state, for example, its undeformed or non-tensioned state. As used herein, the "pitch" of a helical anchor is the distance from the center of one coil to the center of an adjacent coil. In a typical helix, the coils extend in a same axial direction, such that each coil can be said to have a positive pitch with respect to a preceding coil in this axial direction. However, if one of the turns or coils doubles over on an outside or an inside of its preceding coil, then it could be said that that particular coil extends in a direction opposite to the positive axial direction, making the pitch of that coil "negative" relative to its preceding coil. Thus, a coil with a "negative pitch" extends along the longitudinal axis of the helical anchor in a direction opposite to the direction of extension of the other coils in the helical anchor. In some embodiments, a helical anchor can be pre-formed with at least one coil having a negative pitch relative to other coils in the anchor when the anchor is in its undeformed or non-tensioned state. In these embodiments, when the helical anchor is held in a tensioned stated, the pitch as measured from a first coil to a second coil extends in a first direction and defines a positive pitch, and when the helical anchor is released from the tensioned state, the second coil can move axially back towards and past the first coil, such that the second coil extends in the opposite direction and defines a negative pitch. As such, the first coil can be disposed at least partially within (i.e., radially inward from) the second coil, or vice versa, in such a non-tensioned state. The anchor can be adjusted to its final position by self-aligning or by being guided or installed by the delivery system.

FIGS. 2A-3B show a helical docking device 34 according to a first embodiment of the invention. The docking device 34 includes first and second lower or ventricular coils 54a, 54b configured to be positioned on the ventricular side of the native valve, and first and second upper or atrial coils 56a, 56b configured to be positioned on the atrial side of the native valve. Although the illustrated docking device 34 has two ventricular coils and two atrial coils, other embodiments of the docking device can have a greater or fewer number of ventricular coils and/or atrial coils.

In the embodiment of FIGS. 2A-3B, the atrial coils 56a, 56b have an inner diameter that is different than the inner diameter of the ventricular coils 54a, 54b, to facilitate nesting or positioning of the atrial coils within the ventricular coils when the docking device 34 is in a compressed state. As shown in FIGS. 2B-2C, the atrial coils 56a, 56b have an inner diameter 72 that is less than the inner diameter 74 of the ventricular coils 54a, 54b. Larger ventricular coils can, for example, make it easier to loop the ventricular coils 54a, 54b around the leaflets of the native mitral valve and/or the chordae tendineae. Larger ventricular coils can also, for example, allow the docking device and a docked prosthetic heart valve to be placed higher in the native valve (i.e., towards the atrium), as further described below.

Figure 3A:
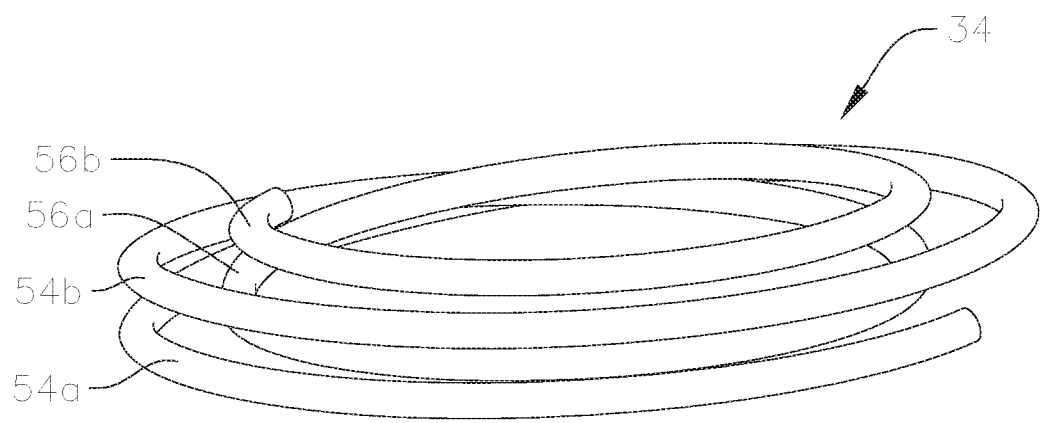
FIGS. 3A and 3B respectively show a perspective view and a cross-sectional view of a compressed state of the helical device of FIGS. 2A-2C.
Figure 3B:
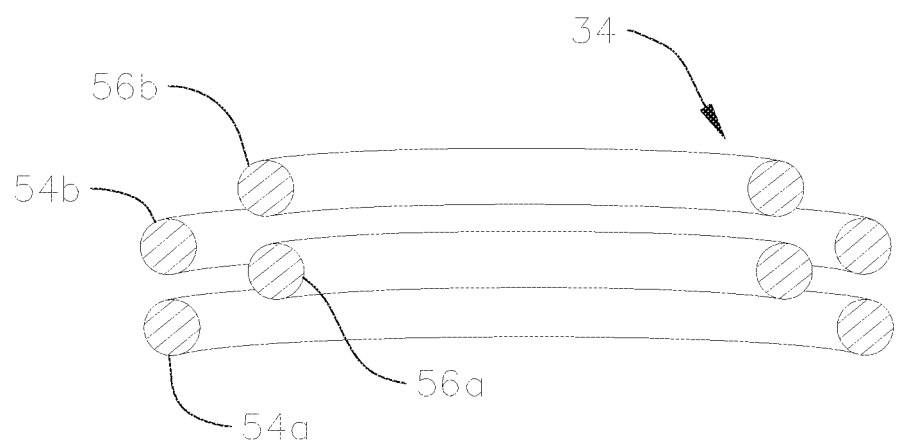

The atrial coils 56a, 56b can have an inner diameter 72 of about 22 mm to about 30 mm, with about 25 mm being a specific example. The ventricular coils can have an inner diameter 74 of about 24 mm to about 32 mm, with about 27 mm being a specific example. The coil wire can have a diameter of about 0.3 mm to about 1.2 mm, with about 1 mm being a specific example. When the docking device 34 is in the axially compressed state (e.g., as seen in FIGS. 3A-3B), the innermost diameter of the docking device can be about 25 mm, and the outermost diameter of the docking device can be about 29 mm. The prosthetic valve 36 can be selected to have a nominal outer diameter that is slightly larger than the innermost diameter of the docking device to create sufficient anchoring force between the prosthetic valve and the docking device in the radial direction to hold the prosthetic valve in place. For example, a docking device having the dimensions provided above can be used with a 26 mm prosthetic valve.

In alternative embodiments, the inner diameter of the atrial coils can be greater than the inner diameter of the ventricular coils (e.g., as seen in FIGS. 6A-6D, described in greater detail below).

In particular embodiments, the inner diameter of each ventricular coil can be substantially the same, and/or the inner diameter of each atrial coil can be substantially the same. As such, when the docking device 34 moves from the axially expanded state to the axially compressed state, as further described below, the ventricular coils 54a, 54b axially overlap with the atrial coils 56a, 56b in a manner similar to a cylinder within a cylinder.

In other embodiments, the inner diameter of each of the atrial and ventricular coils can vary. For example, an atrial coil can have an inner diameter that is greater than or less than the inner diameter of another atrial coil, and a ventricular coil can have an inner diameter that is greater than or less than the inner diameter of another ventricular coil. In addition, one or more atrial coils can have an inner diameter that is the same as one or more ventricular coils.

Figure 2A:
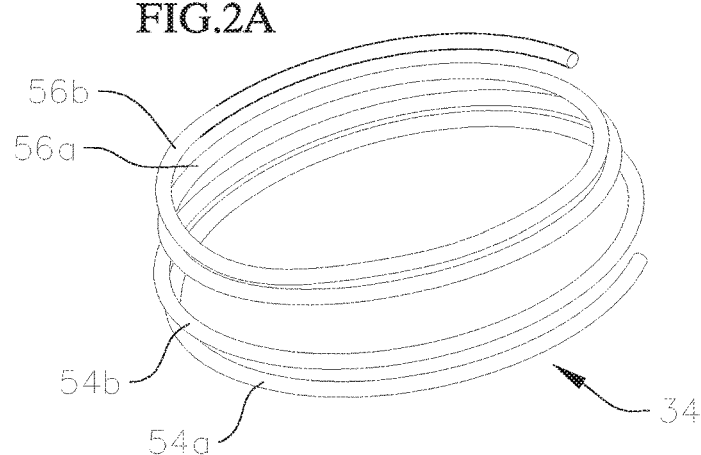
FIGS. 2A-2C respectively show a perspective view, a side view, and a top view of a helical device according to a first embodiment of the invention.
Figure 2B:
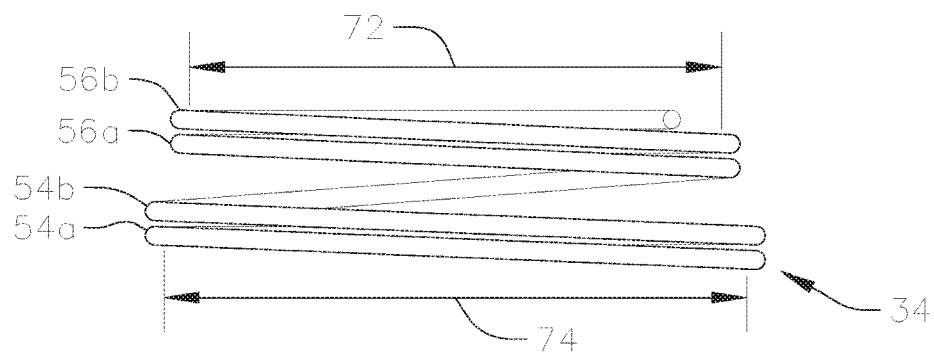
Figure 2C:
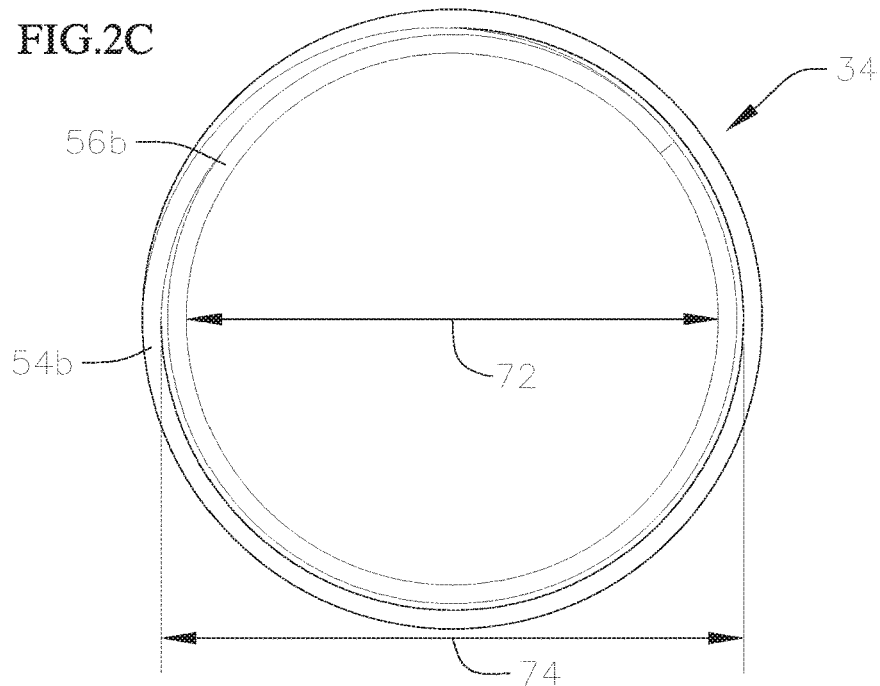

In one embodiment, docking device 34 is axially expandable when tension is applied to one or both ends of the docking device 34, and is axially compressible when tension is released from the docking device 34. In this manner, the docking device 34 can be said to be made up of or act similarly to a tension spring. FIGS. 2A-2C show the docking device in an axially expanded state such that all the coils have a positive pitch with respect to adjacent coils. That is, the second ventricular coil 54b is located upstream of the first ventricular coil 54a in the axial direction (i.e., upwards as illustrated), the first atrial coil 56a is located upstream of the second ventricular coil 54b, and the second atrial coil 56b is located upstream of the first atrial coil 56a. Therefore, in this embodiment, a positive pitch direction can be defined as being oriented in the upstream or upwards direction.

Meanwhile, FIGS. 3A-3B show the docking device 34 in an axially compressed state, for example, after tension is released from the docking device 34. In this state, the first atrial coil 56a moves, or is activated by a delivery system, axially past the center of the second ventricular coil 54b in the downstream direction (i.e., downwards as illustrated), such that the first atrial coil 54a is located below the second ventricular coil 54b (and between the first ventricular coil 54a and the second ventricular coil 54b in the embodiment shown). Thus, the first atrial coil 56a can be said to be positioned at a negative pitch with respect to the second ventricular coil 54b. Additionally, in the compressed state, the atrial coils 56a, 56b are located radially inward of the ventricular coils 54a, 54b. As shown, the atrial coils 56a, 56b become interlaced and nest within the ventricular coils 54a, 54b.

By virtue of the docking device 34 assuming the axially compressed state shown in FIGS. 3A-3B, the native valve leaflets can become captured between the ventricular coils 54a, 54b and the atrial coils 56a, 56b (see, e.g., FIGS. 4L and 4M), with the coils compressing or pinching the leaflets between adjacent coils in the radial direction, and in some cases in the axial direction as well. The docking device 34 exerts sufficient force against the native leaflets to retain the docking device 34 in place and resist migration due to the flow of blood between the left atrium and the left ventricle, before a prosthetic heart valve is implanted within the docking device 34. Because the docking device 34 can be secured to the valve leaflets without needing to be held in place by a delivery apparatus or other device, the delivery apparatus can be removed from the patient's heart prior to deploying a prosthetic heart valve within the docking device 34, as further described below. This can, for example, advantageously reduce the complexity of the entire procedure of implanting the docking device and the prosthetic heart valve thereafter.

Since at least some coils of the docking device 34 axially overlap (similar to a spring within a spring) the docking device can be formed from a relatively thin wire. This is because together, the axially-overlapping coils provide sufficient radial force to securely hold a prosthetic heart valve in place during the dynamic diastolic and systolic phases of heart contraction. Forming the docking device from a relatively thin wire can, for example, make the docking device 34 easier to deliver through a delivery apparatus and can facilitate deployment from the delivery apparatus.

The docking device 34 can be shaped or otherwise formed from a piece of wire, tube, or strip of material that is made from a flexible, elastic, resilient material such as Nitinol, stainless steel, or a polymer that returns to its original shape when released from a deformed or deflected state. Coil flexibility can also, for example, be achieved by using a narrow or thin spring, applying notches to a thin tube, or using a braided material. In some embodiments, the docking device can be loaded into the shaft of a delivery catheter and retained in a substantially straight configuration within the delivery catheter for delivery into the heart of a patient. When formed from a flexible, elastic, resilient material, the docking device 34 can be formed or shape-set (e.g., by heat-shaping a Nitinol wire) in the helical, axially compressed state shown in FIG. 3A. In this manner, the docking device 34 can transition from the substantially straight configuration to its coiled configuration after it is released from the delivery catheter.

As shown, the coil wire of docking device 34 has a generally circular cross-sectional shape. In other embodiments, the coil wire can include various other cross-sectional shapes, such as square, rectangular, elliptical, etc. For example, the coil wires of docking device 300 and docking device 400 (see FIGS. 7A-7C and 8A-8C) have a generally rectangular cross-sectional shape.

It should be noted that a docking device can be formed from one or more helically-shaped pieces of wire, tubes, or strips of material. For example, in some embodiments, the ventricular coils and the atrial coils can be formed from one continuous piece of wire. In other embodiments, the ventricular coils can be formed from a first piece of wire or material, and the atrial coils can be formed from a second, separate piece of wire or material. When the docking device is formed from two or more pieces of wire or material, each piece of the docking device can, for example, be deployed using the same delivery apparatus or using separate delivery apparatuses.

In embodiments discussed above, at least part of a first set of coils becomes nested within a second set of coils, where at least a portion of one or more coils of the second set align or overlap with one or more coils of the first set in a radial direction, for example, by virtue of releasing tension on the docking device and allowing the device to assume a shape-memory state. In other embodiments, a docking device can be configured such that the atrial coils and the ventricular coils do not revert to a nested configuration when tension is released from the docking device. Instead, the docking device can be configured such that a first set of coils are manually moved to an axial position where one or more coils of the second set overlap one or more coils of the first set in the radial direction, such as by application of an axially directed force to one or both ends of the docking device. In these embodiments, the docking device can, for example, be forced into the nested or radially overlapping state by manually applying a force (e.g., an axially compressive force) to the docking device with a delivery apparatus.

FIGS. 4A-4M show a method of implanting a docking device 34 and a prosthetic heart valve 36 at a native mitral valve 42 of a patient's heart 12 with a delivery apparatus 10, according to one embodiment that uses a transventricular technique.

Figure 4A:
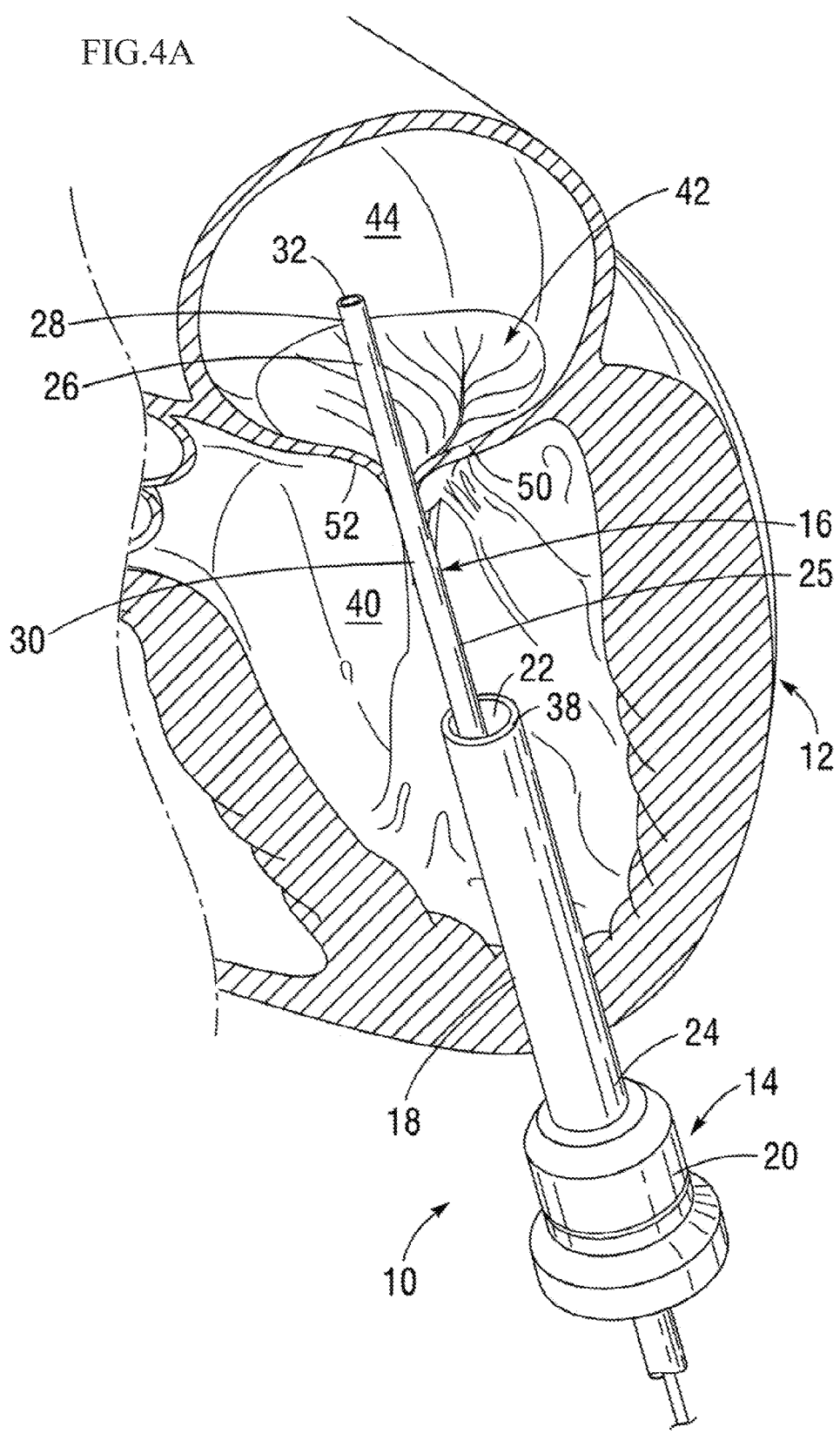

As shown in FIG. 4A, the delivery apparatus 10 includes an introducer 14 and a flexible delivery catheter 16 (also referred to as a "guide catheter" in some embodiments). The introducer 14 of the delivery apparatus 10 has an axially extending shaft portion 18 and a hub or housing 20. The housing 20 is fixedly secured or coupled to the proximal end 24 of the shaft portion 18. The introducer 14 also has a lumen 22 extending co-axially through the shaft 18 and the housing 20. Through the lumen 22 of the introducer 14, various other components of the delivery apparatus 10 and/or other devices (prosthetic implants, catheters, etc.) can be introduced into the patient's heart 12. The housing 20 can also house one or more elastomeric seals to maintain hemostasis as devices are inserted through the lumen 22, as known in the art.

The guide catheter 16 of the delivery apparatus 10 includes an elongate shaft 25. The shaft 25 has a flexible section 26 extending along a distal portion of the shaft 25, a relatively more rigid section 30 located adjacent and proximal to the flexible section 26, and a lumen 32 that extends the length of the shaft 25.

The flexible section 26 of the shaft 25 can be positioned in a first, delivery configuration and a second, activated configuration. In the delivery configuration, the flexible section 26 is substantially straight, allowing the flexible section 26 to easily pass through the lumen 22 of the introducer 14 and the mitral valve 42, as shown in FIG. 4A. In the activated configuration, the guide catheter 16 forms a first, "U"-shaped curved portion 46 and a second, helically curved portion 48, as best shown in FIGS. 4B and 4C. The first curved portion 46 forms a 180-degree bend at the end of the rigid section 30 and extends substantially parallel to the rigid section 30. The second curved portion 48 includes a proximal section 48a that curves radially away from the first curved portion 46 in a plane that is substantially perpendicular to the first curved portion 46 and includes a distal tip portion 48b that is angled downwardly away from the plane of the proximal section 48a. These curved portions 46, 48 can help properly position the helical docking device 34 during the implantation procedure, as further described below.

In one embodiment, the flexible section 26 of the shaft 25 can be formed from a flexible, elastic, resilient material such as Nitinol or a polymer that returns to its original shape when released from a deformed or deflected state. When formed from a resilient material, the flexible section 26 of the shaft 25 can be formed or shape-set (e.g., by heat-shaping a Nitinol tube) in the activated configuration (as seen in FIG. 4B). In this manner, the curved, activated configuration is the undeformed state of the flexible section, and therefore the flexible section will assume the activated configuration in the absence of any external forces applied to the shaft.

Due to its flexible nature, the flexible section 26 of the shaft 25 can be retained in the delivery configuration shown in FIG. 4A, for example, by inserting a rigid rod (not shown)

through the lumen 32 of the shaft 25. Inserting the rigid rod through the lumen 32 of the shaft 25 forces the flexible section 26 of the shaft 25 to axially elongate or straighten, thus reducing the radial profile of the distal end of the guide catheter 16 compared to the radial profile of the distal end of the guide catheter 16 in the activated configuration. The delivery configuration can allow the guide catheter 16 to move more easily through the patient's vasculature. Once the flexible section 26 of the shaft 25 has been advanced into the left atrium of the heart, the rigid rod can be retracted from within the flexible section 26 of the shaft 25, which allows the flexible section 26 to return to its curved, activated configuration.

In an alternative embodiment, the flexible section 26 of the shaft 25 can be placed in its activated configuration by one or more actuators or steering mechanisms. For example, the flexible section 26 can be converted from the delivery configuration to the activated configuration using at least one pull wire (see, e.g., pull wire 104 in FIGS. 9A-9C). The pull wire can extend co-axially through the lumen 32 of the shaft 25 and can have a distal end fixedly secured to the inner surface of the distal end 28 of the shaft 25. The flexible section 26 of the shaft 25 can be configured such that pulling on the proximal end of the pull wire, while maintaining the axial positioning of the guide catheter 16, applies an axially compressive force to the guide catheter 16. This axially compressive force causes the flexible section 26 of the shaft 25 of the guide catheter 16 to bend from the delivery configuration into the activated configuration based, for example, on specific cuts or slots formed along the length of the shaft 25 to control the shaping of the flexible section 26.

In another embodiment, the docking device itself can be used to effect the transition of the flexible section 26 of the shaft 25 from the delivery configuration to the activated configuration. Once the guide catheter 16 is advanced into the desired location for the placement of the docking device, the docking device can be advanced through the lumen 32 of the shaft 25. In this alternative embodiment, the relatively more rigid section 30 of the shaft 25 can be configured to resist the spring force exerted by the docking device 34 (which is attempting to return to its undeformed, helical configuration), while the flexible section 26 of the shaft 25 can be configured to yield under the spring force exerted by the docking device 34. As a result, as the docking device 34 is advanced through the lumen 32 of the shaft 25, the rigid section 30 maintains its shape, while the flexible section 26 is caused to assume its activated configuration under the force of the docking device 34.

In some embodiments, the flexible section 26 and the rigid section 30 can be formed from the same material and/or formed from a single piece of material (e.g., an alloy tube). When formed from the same material and/or from a single piece of material, the shaft can be formed (e.g., laser cut) with a series of slots in selected locations to impart a desired shape and degree of flexibility along certain portions of the flexible section and/or to achieve the curvature of the curved portions 46, 48 when the shaft is in the activated configuration. In other embodiments, the flexible section 26 and the rigid section 30 can be formed from different materials and/or formed from separate pieces of the same material that are fixedly secured or coupled together by an adhesive, welding, fasteners, etc. Materials having varying flexibility can be selected to form different sections of the shaft to achieve the desired degree of flexibility for each section of the shaft.

Also, although not shown, it should be noted that the guide catheter 16 can have multiple radial layers. For example, the delivery catheter 16 can have an inner tube made of Nitinol, stainless steel, plastic, or other suitable material, that is surrounded by a polymeric cover (e.g., PTFE). The delivery catheter 16 can also be formed from an alloy or metal mesh or weave (e.g., braided Nitinol) having an inner and/or outer polymeric liner. The interior of the delivery catheter can be lined with a lubricious material (e.g., PTFE) to allow the other devices to pass more easily through the lumen 32 of the shaft 25.

Referring back to FIGS. 4A-4C, the distal end 38 of the shaft 18 of the introducer 14 can be inserted through the wall of the left ventricle 40, for example, at or near the apex of the heart, until the distal end 38 is positioned in the left ventricle 40. The positioning of the delivery apparatus 10 and later, the docking device 34 and the prosthetic valve 36, can be confirmed visually, for example, by using imaging modalities such as fluoroscopy, X-ray, CT, or MR imaging. Echocardiography in either 2D or 3D can also be used to help guide and adjust the positioning of the delivery apparatus 10, the docking device 34, and the prosthetic valve 36.

Although not shown, a standard purse string suture can be used to hold the introducer 14 in place against the heart 12 and to prevent blood leakage around the introducer 14, as well as to seal the opening in the heart 12 upon removal of the introducer 14. As noted above, the introducer 14 can include an internal sealing mechanism (e.g., hemostasis seal) to prevent blood leakage through the lumen 22 of introducer 14.

With the flexible section 26 of the shaft 25 in the delivery configuration (i.e., straight or substantially straight), the delivery catheter 16 can then be inserted into the patient's heart 12 by advancing the distal end 28 of the shaft 25 through the lumen 22 of the introducer 14, such that the flexible section 26 extends through the left ventricle 40 and the mitral valve 42 into the left atrium 44 of the heart 12. The flexible section 26 of the shaft 25 can then be moved or adjusted to the activated configuration, as described above.

As shown in FIGS. 4B-4C, the delivery catheter 16 can then be rotated in the direction shown by arrow 58, causing the distal end 28 of the shaft 25 to move laterally over the posterior leaflet 50 towards the coaptation edges of the leaflets 50, 52. The distal end 28 of the shaft 25 can then be positioned under the anterior leaflet 52 (e.g., desirably near the A3 and P3 regions of the leaflets, as identified by Carpentier nomenclature) such that the lumen 32 of the shaft 25 opens into the ventricular side of the anterior leaflet 52, while the helically curved portion 48 and the "U"-shaped portion 46 remain on the atrial side of the leaflets 50, 52, as shown in FIGS. 4D-4E.

Figure 4F:
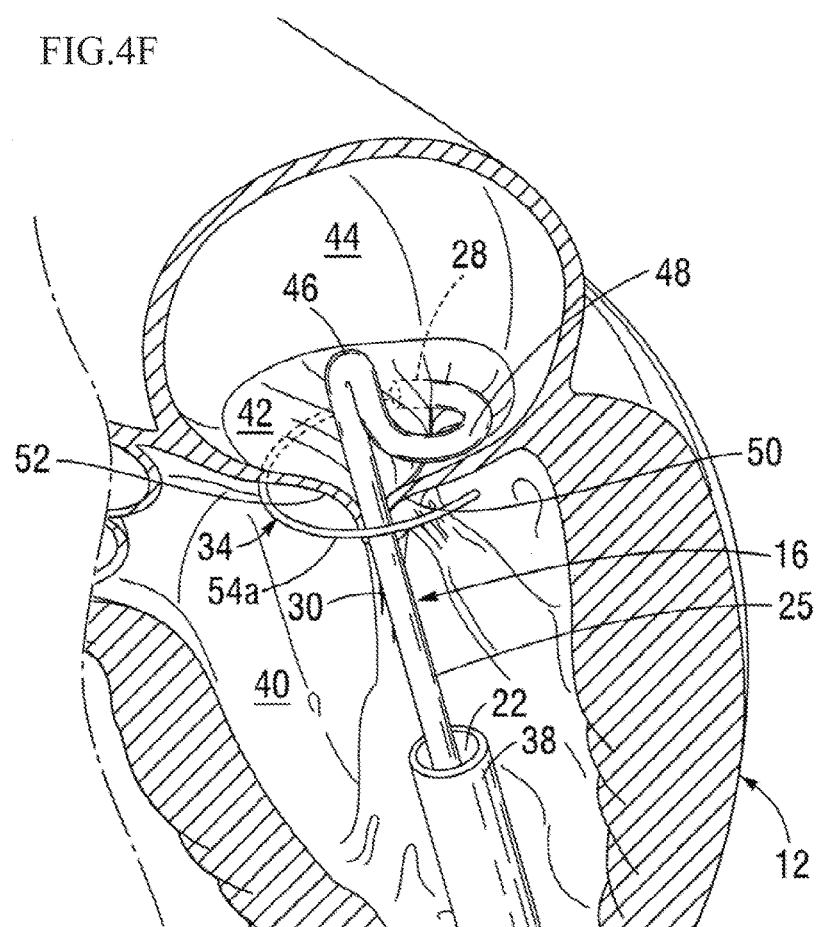
Figure 4G:
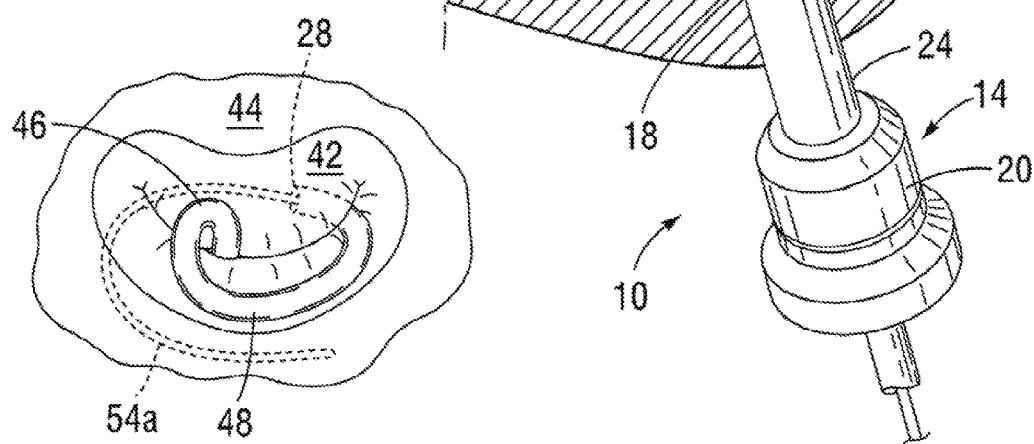
Figure 4H:
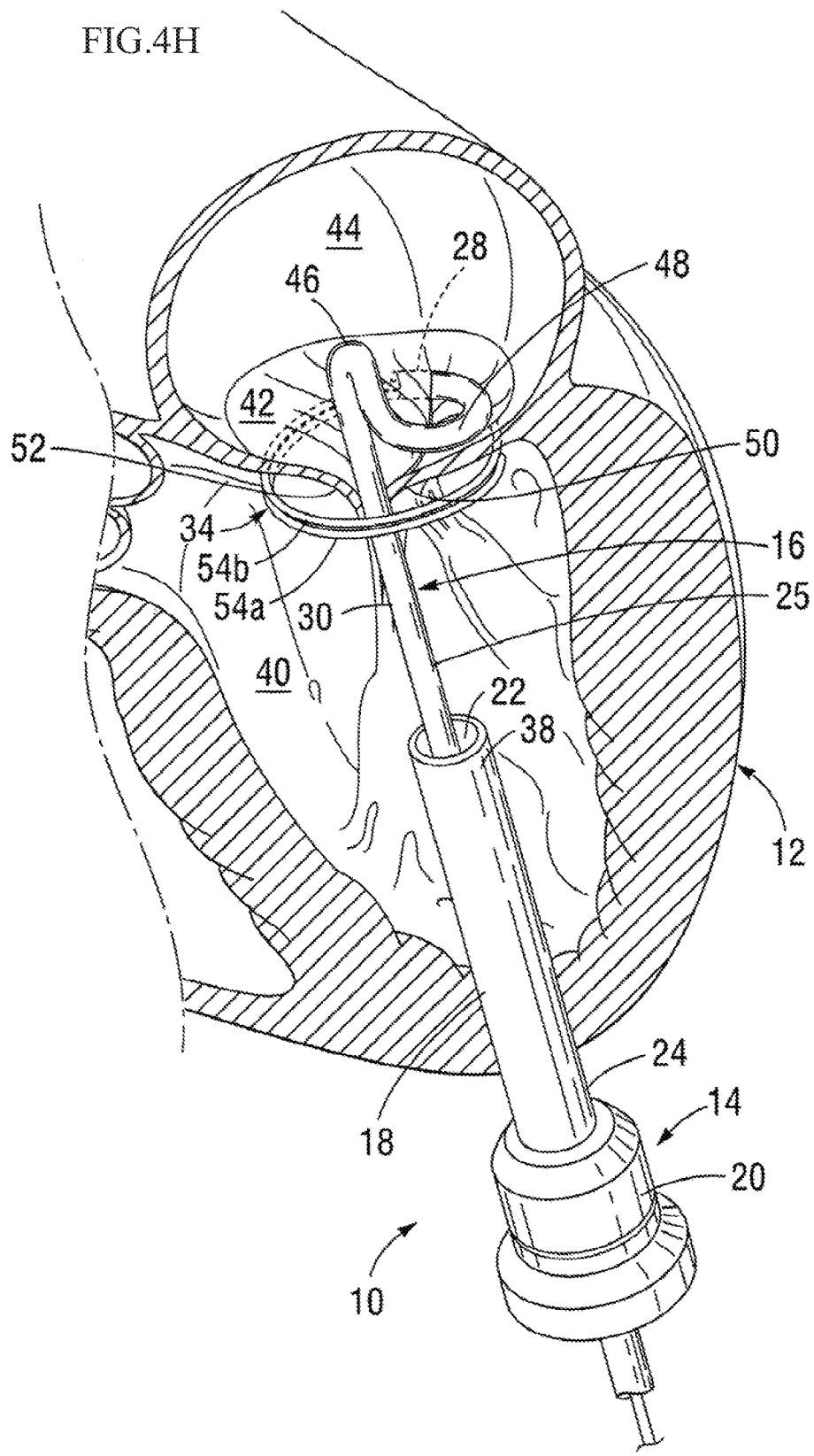

With the delivery catheter 16 in the position shown in FIGS. 4D-4E, the docking device 34 can be advanced through the lumen 32 of the shaft 25 such that the first ventricular coil 54a extends from lumen 32 into the left ventricle 40 of the patient's heart. Due to the flexible and elastic nature of the docking device 34, the docking device 34 can assume a coiled or helical configuration as it exits the lumen 32 of the shaft 25. For example, as the first ventricular coil 54a is advanced from the lumen 32 of the shaft 25, the first ventricular coil 54a tracks under the leaflets 50, 52 and advances around the rigid section 30 of the shaft 25, as shown in FIGS. 4F-4G. As the docking device 34 is further advanced through the lumen 32 of the shaft 25, the second ventricular coil 54b also tracks under the leaflets 50, 52 and advances around the rigid section 30 of the shaft 25 above the first lower turn 54a, as shown in FIG. 4H.

Figure 4I:
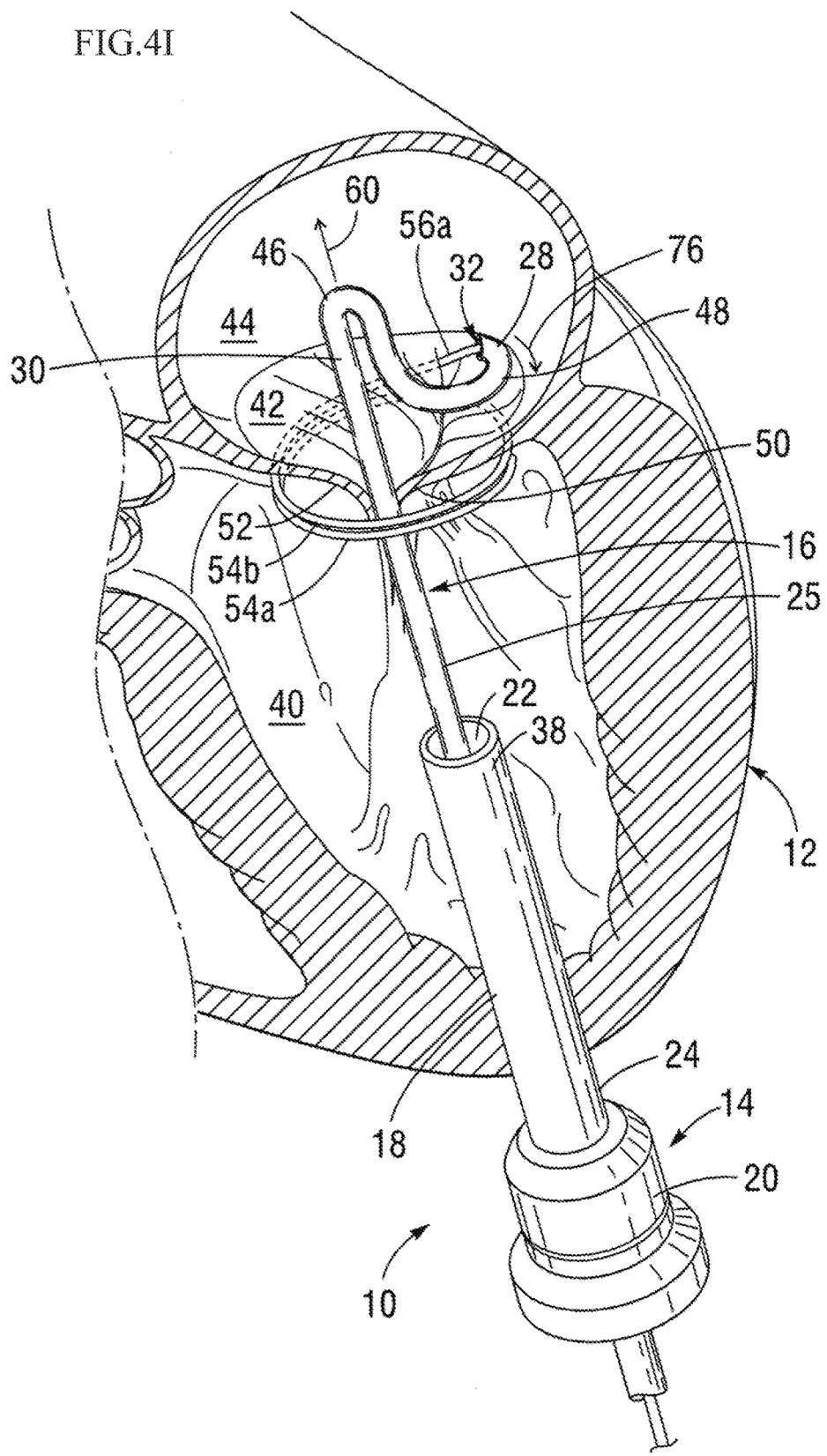

With the ventricular coils 54 of the helical docking device 34 positioned under the leaflets 50, 52, the delivery catheter 16 can then be rotated in the direction of arrow 76 in FIG. 4I, such that the distal end 28 and lumen 32 of the shaft 25 is rotated back and again opens into the atrial side of the leaflets 50, 52, in order to deploy the atrial coils 56a, 56b from the distal end 28 of the shaft 25. The delivery catheter 16 can also be advanced upwardly in the direction of arrow 60 into the left atrium 44, to apply a small amount of tension to the docking device against the native mitral valve as the atrial coils 56a, 56b are deployed. Positioning the delivery catheter 16 in this manner allows the atrial coils 56a, 56b to deploy on the atrial side of the mitral valve 42, while the tension holds the atrial coils 56a, 56b spaced slightly above the native leaflets.

Figure 4J:
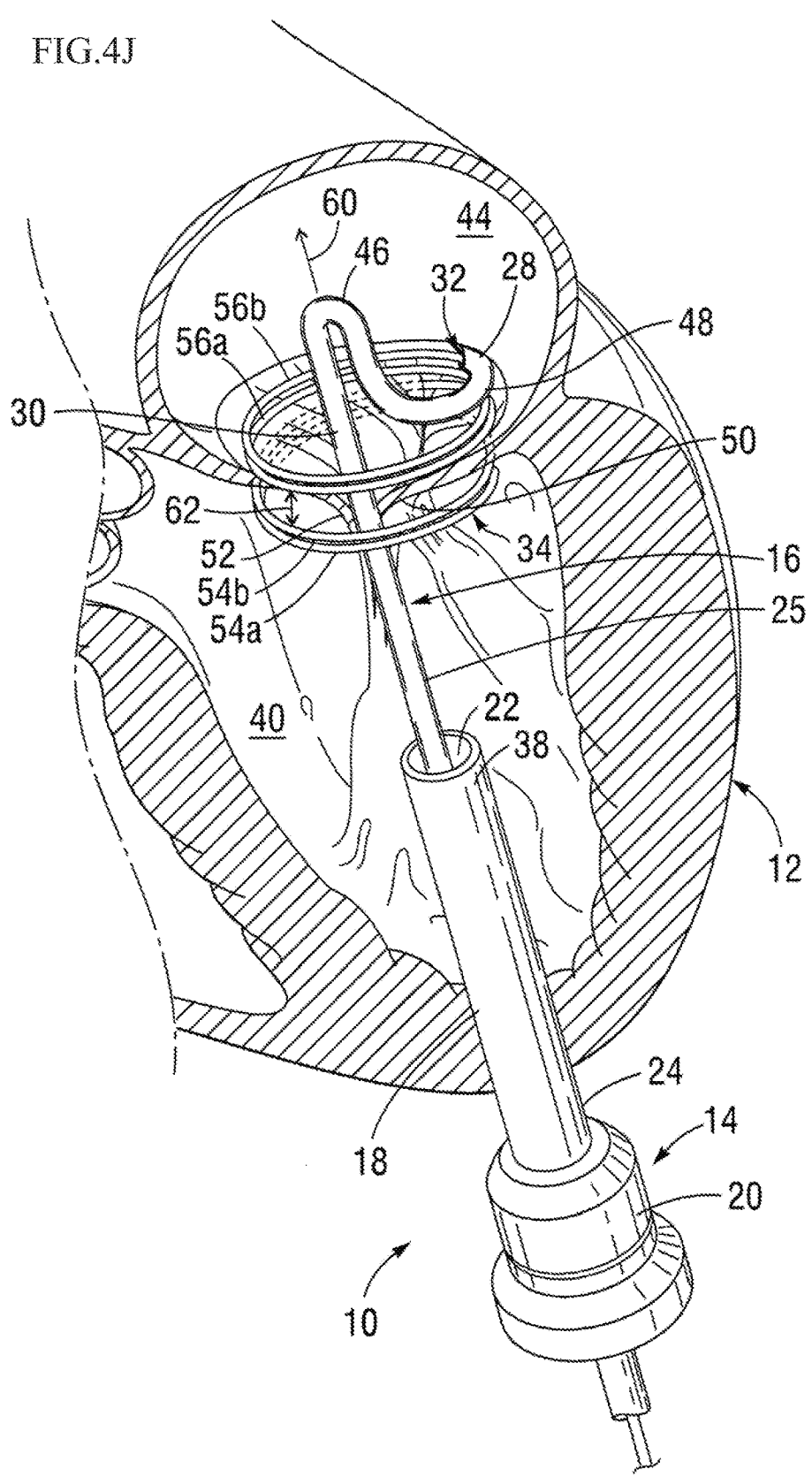

The atrial coils 56a, 56b can then be fully deployed, for example, by continuing to rotate the delivery catheter 16 in the direction of arrow 76 to further release the docking device 34 from the lumen 32 of the shaft 25. FIG. 4J shows the first and the second coils 56a, 56b, respectively, extending around the delivery catheter 16 on the atrial side of the mitral valve 42. During this deployment, an axial space 62 and a positive pitch between the second ventricular coil 54b and the first atrial coil 56a remains, as shown in FIG. 4J. FIG. 4K is a schematic cross-sectional view showing the docking device 34 when it is still in a partially axially expanded state.

Fully deploying the docking device 34 from the delivery catheter 16 releases the tension on the docking device 34, allowing the atrial coils 56a, 56b to move axially downward towards the ventricular coils 54a, 54b. The ventricular coils 54a, 54b may also move axially upward towards the atrial coils 56a, 56b. In this manner, the docking device 34 moves toward its axially compressed state, as shown in FIG. 4L. As the atrial coils 56a, 56b nest within the ventricular coils 54a, 54b, the native leaflets 50, 52 become captured between the ventricular coils on the ventricular side of the native leaflets and the atrial coils on the atrial side of the native leaflets. Securing the docking device 34 to the native leaflets 50, 52 with the native leaflets compressed or pinched axially and radially between the coils can assist the docking device to better maintain its positioning relative to the native leaflets, compared to coils that can only apply axially directed forces against the captured leaflets.

By virtue of the axially compressed state of the docking device 34 and by deploying the atrial coils 56a, 56b in the manner described, the docking device 34 can also achieve a relatively high anchoring position (e.g., the second atrial coil 56b can be positioned close to or higher than the annulus of the mitral valve 42). Positioning the docking device at a relatively high position can, for example, help avoid or reduce left ventricle outflow tract (LVOT) occlusion, as well as chordae and/or left ventricle damage or leakage due to insufficient leaflet coaptation.

Once the docking device 34 is secured to the native leaflets 50, 52, the delivery catheter 16 can be removed from the patient's heart 12, for example, by straightening the flexible section 26 of the shaft 25 and retracting the delivery catheter 16 through the lumen 22 of the introducer 14. The flexible section 26 of the shaft 25 can, for example, be straightened by advancing a rigid rod through the lumen 32 of the shaft 25 into the flexible section 26, or by adjusting one or more pull wires.

With the delivery catheter 16 removed, a prosthetic valve 36 can then be introduced into the patient's heart 12. As shown in FIG. 4L, the prosthetic valve 36 can be mounted on an inflatable balloon 66 of a balloon catheter 64. However, the prosthetic valve 36 can be any plastically-expandable prosthetic valve that can be mounted in a radially compressed state on an expansion mechanism of a valve delivery catheter. Alternatively, the prosthetic valve can be a self-expanding prosthetic valve that can be retained in a radially compressed state within a sheath of a delivery catheter, or a mechanically-expandable valve.

The prosthetic valve 36 can be introduced into the heart via any known delivery techniques or methods. In the illustrated example, the balloon catheter 64 is inserted through the introducer 14 and into the heart 12 in a transventricular approach. In other embodiments, the balloon catheter can instead be advanced transfemorally (via a femoral artery and the aorta), transseptally (via the superior or inferior vena cava and through the septal wall between the right and left atrium), transatrially (via a surgical opening in the left atrium), or by other methods and/or via other access points.

The balloon catheter 64 is advanced distally through the introducer 14 until the prosthetic valve 36 is positioned within the docking device 34. Once positioning of the prosthetic valve 36 is confirmed, the prosthetic valve 36 is radially expanded to its functional size and secured to the helical docking device 34 by inflating the balloon 66 of the balloon catheter 64. In the case of a self-expanding prosthetic valve, the prosthetic valve is advanced distally out of the distal opening of a sheath of the delivery catheter, or the sheath is retracted, allowing the prosthetic valve to self-expand to its functional size.

The prosthetic valve 36 can be selected to have a nominal outer diameter in its radially expanded state that is slightly larger than the inner diameter of the atrial coils 56a, 56b. As a result, when the prosthetic valve 36 is radially expanded to its functional configuration within the docking device 34, the outer surface of the prosthetic valve 36 is forced radially against the inner diameter of the atrial coils 56a, 56b, thereby radially compressively securing the prosthetic valve within the docking device 34.

Figure 4M:
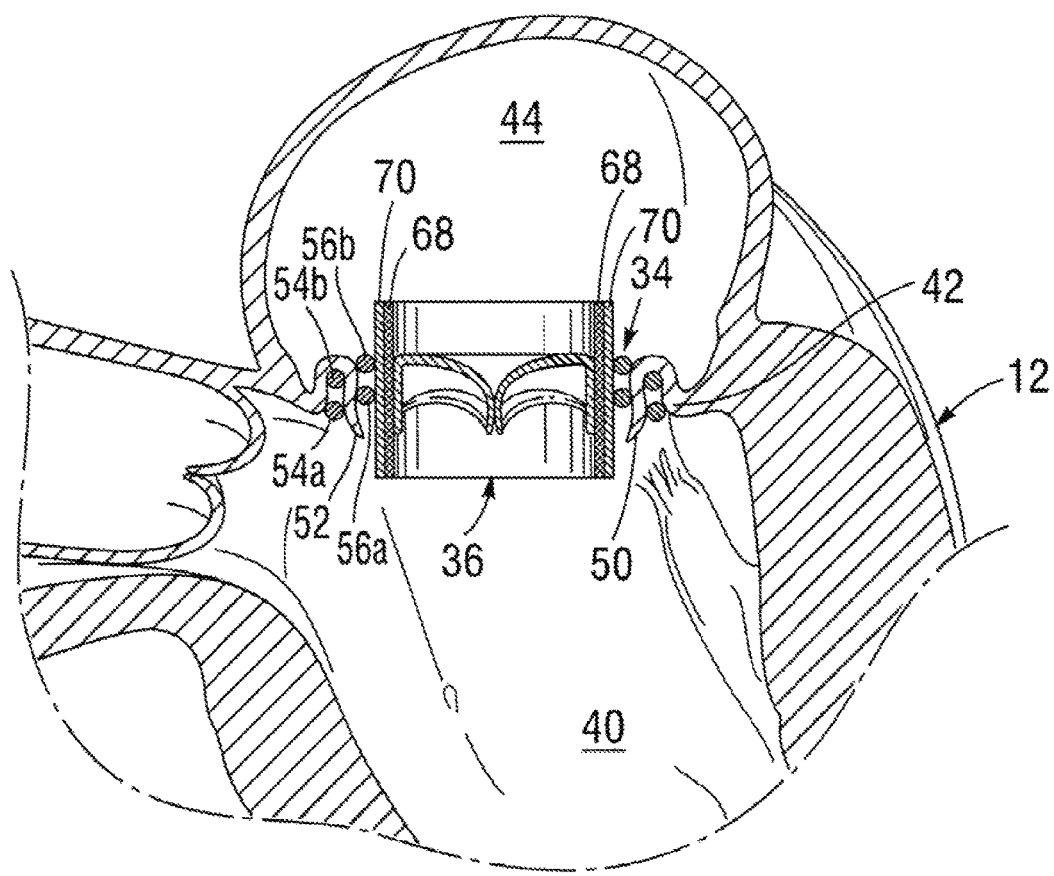

As shown in FIG. 4M, the prosthetic valve 36 can also include a blood impervious outer covering or sealing member 70 (also referred to in certain embodiments as an "outer skirt") extending over the metal frame 68 of the prosthetic valve. The sealing member 70 can be made of or include, for example, any of various biocompatible fabrics (e.g., PET) or natural tissue (e.g., pericardium tissue). The sealing member 70 can help create a seal between the prosthetic valve and the docking device to minimize or prevent paravalvular leakage between the prosthetic valve and the docking device. Similarly, the docking device 34 can include an outer sealing layer (not shown) covering the coil wire to further enhance the sealing between the prosthetic valve and the docking device.

Once the prosthetic valve 36 is secured within the docking device 34, the balloon catheter 64 can be removed from the patient's heart 12 by deflating the balloon 66 and retracting the catheter 64 from the prosthetic valve 36 and the introducer 14. The introducer 14 can then be removed from the patient's heart 12, and the opening in the patient's heart 12 can be closed.

FIGS. 5A-5E show a method of implanting the helical docking device 34 at the native mitral valve 42 of a patient's heart 12 with a delivery apparatus 200, according to another embodiment that uses a transseptal technique.

The delivery apparatus 200 includes an outer catheter 202 and a flexible delivery catheter 204. The outer catheter 202 can have an axially extending shaft 206 and a lumen 208, which extends co-axially through the shaft 206. Through the lumen 208 of the outer catheter 202, various other components (e.g., delivery catheter 204, device 34, etc.) can be introduced into the patient's heart 12.

The delivery catheter 204 of the delivery apparatus 200 forms or includes an elongate shaft 210. The shaft 210 has a flexible section 212 extending along a distal portion of the shaft 210, a relatively more rigid section 214 located adjacent and proximal to the flexible section 212, and a lumen 216 that extends the length of the shaft 210.

Figure 5A:
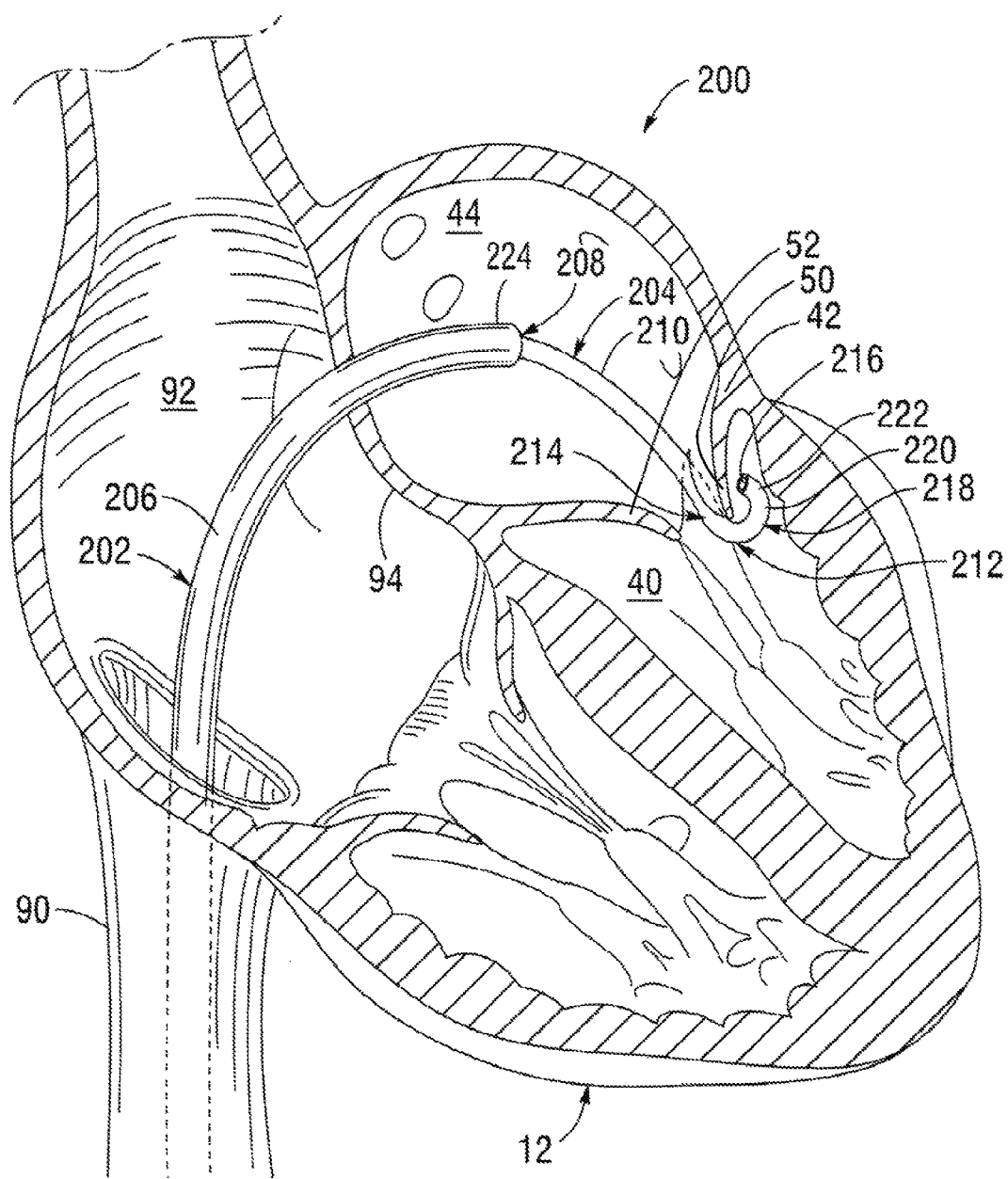
FIGS. 5A-5E show another embodiment of a delivery apparatus and method for implanting a helical device at the native mitral valve of a heart, using a transseptal technique.

The flexible section 212 of the shaft 210 can be positioned or adjusted between a first, delivery configuration and a second, activated configuration. Although not shown, in the delivery configuration, the flexible section 212 is substantially straight, allowing the flexible section 212 to easily pass through the lumen 208 of the outer catheter 202. As best shown in FIG. 5A, in the activated configuration, the delivery catheter forms a helically curved portion 218. The helically curved portion 218 has a proximal section 220 that curves radially away from the shaft 210 in a plane that is substantially perpendicular to the shaft 210, and a distal tip portion 222 that is angled downwardly away from the plane of the proximal section 220. The activated configuration can help position the helical docking device 34 during the implantation procedure, as further described below.

The shaft 210 can be formed from similar materials and can have a construction similar to shaft 25 described above, to effect transitioning of the shaft from the delivery configuration to the activated configuration.

In the transseptal technique shown in FIGS. 5A-5E, first, a distal end 224 of the outer catheter 202 is inserted through a femoral vein and the inferior vena cava 90, and into the right atrium 92. The interatrial septum 94 is then punctured and the outer catheter 202 is passed into the left atrium 44, as can be seen in FIG. 5A. Alternatively, the right atrium 92 can be accessed through the superior vena cava via other access points of the patient's vasculature. The outer catheter can have a steerable or pre-curved distal end portion to facilitate steering of the outer catheter 202 into the left atrium.

With the delivery catheter 204 in the delivery configuration, the delivery catheter 204 is then advanced through the lumen 208 of the outer catheter 202, such that distal tip 222 of the delivery catheter 204 is positioned in the left atrium 44. The delivery catheter 204 is then further advanced through the mitral valve 42 and into the left ventricle 40. As shown in FIG. 5A, the flexible section 212 of the delivery catheter 204 can then be moved into the activated configuration, for example, by allowing the flexible section 212 to assume its shape-set shape or by actively bending the flexible section 212, for example, by using methods similar to those discussed with respect to the delivery catheter described in FIGS. 4A-4M.

Figure 5B:
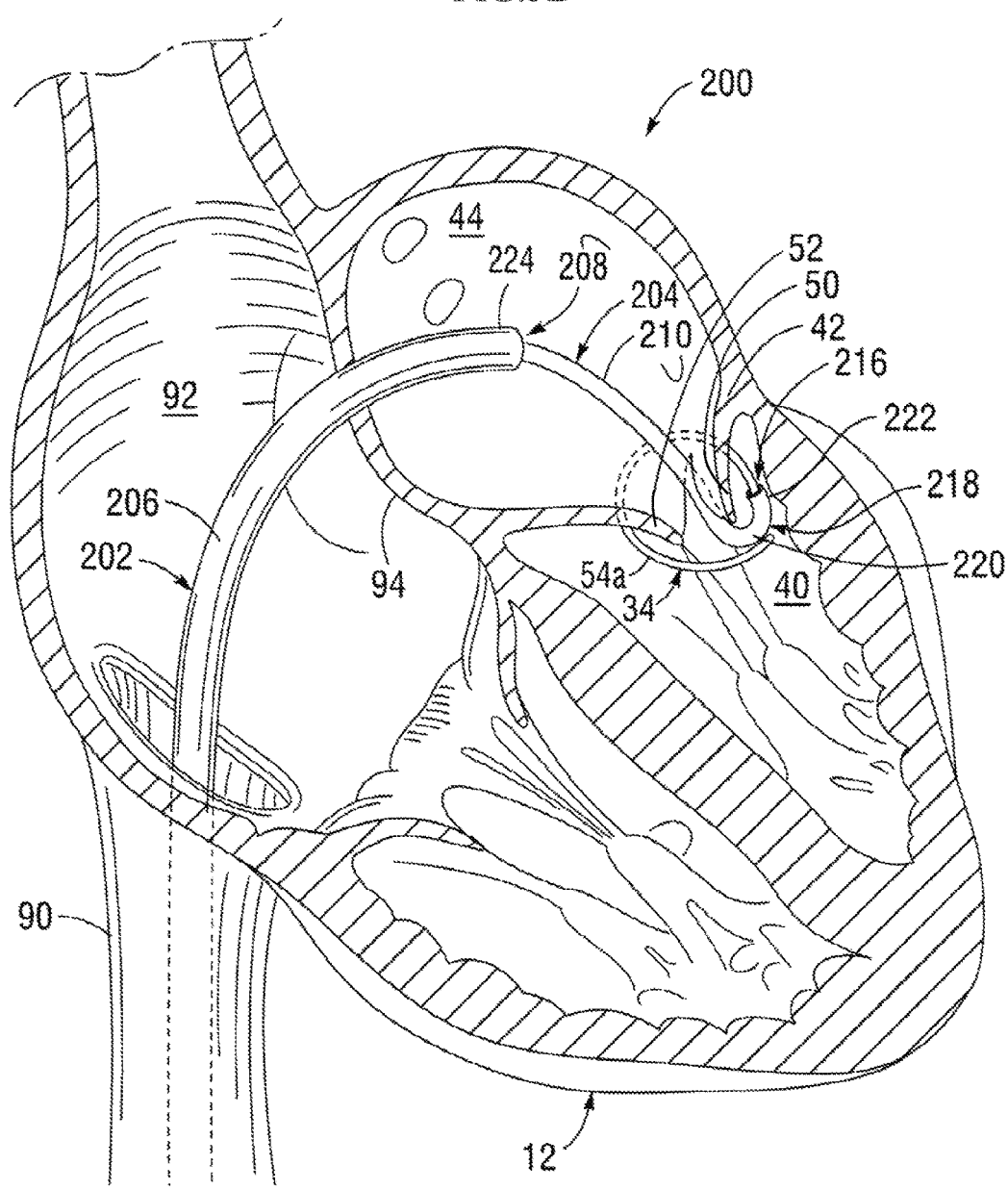
Figure 5C:
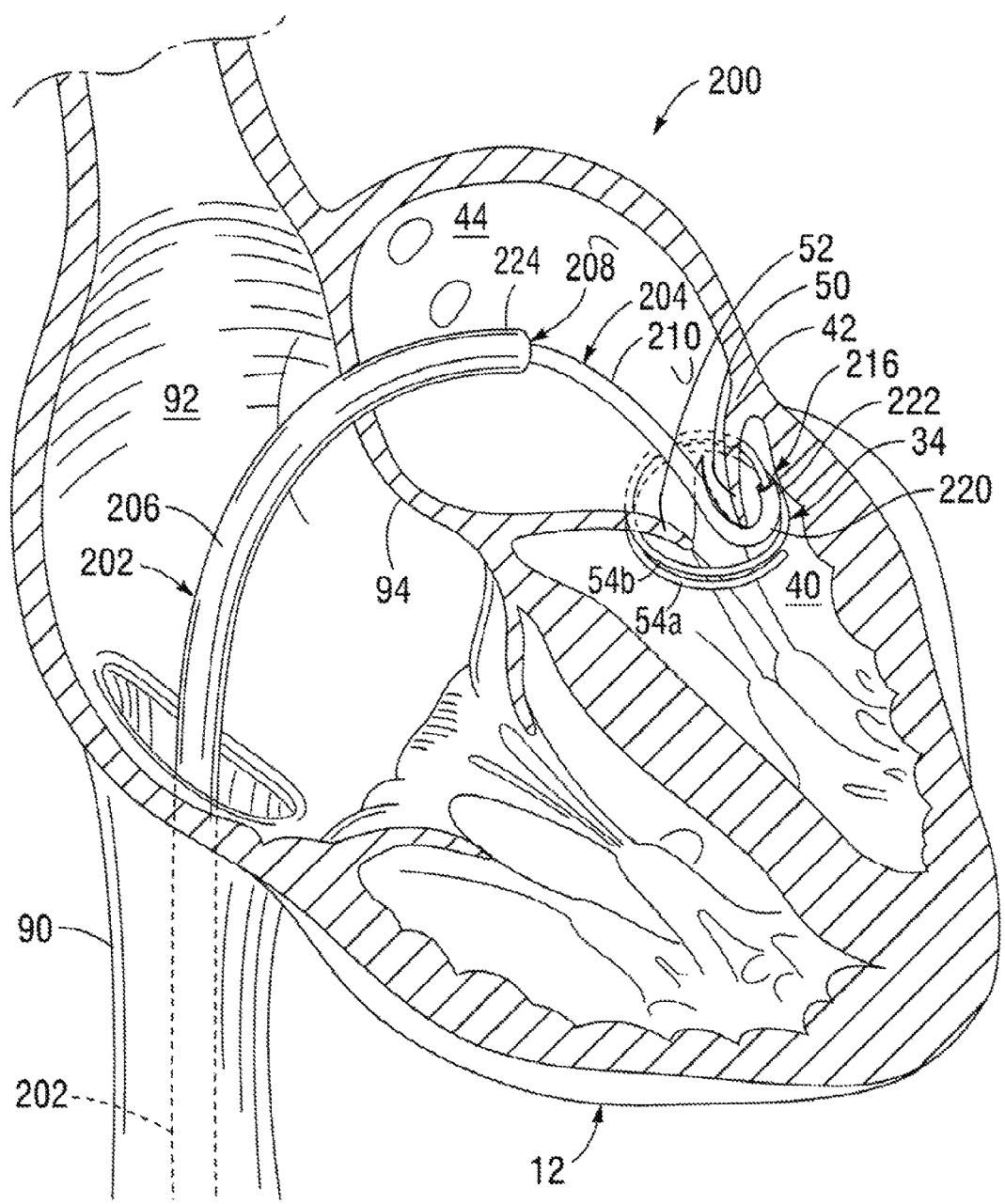

With the delivery catheter 204 in this position, the docking device 34 can be advanced through the lumen 216 such that the first ventricular coil 54a extends from lumen 216 into the left ventricle 40. Due to the flexible and elastic nature of the docking device 34, the docking device 34 can assume a coiled or helical configuration as it exits the lumen 216. For example, as the first ventricular coil 54a is advanced from the lumen 216, the first ventricular coil 54a tracks under the leaflets 50, 52, as best shown in FIG. 5B. As the docking device 34 is further advanced through the lumen 216, the second ventricular coil 54b also tracks under the leaflets 50, 52 and above the first ventricular turn 54a, as shown in FIG. 5C.

Figure 5D:
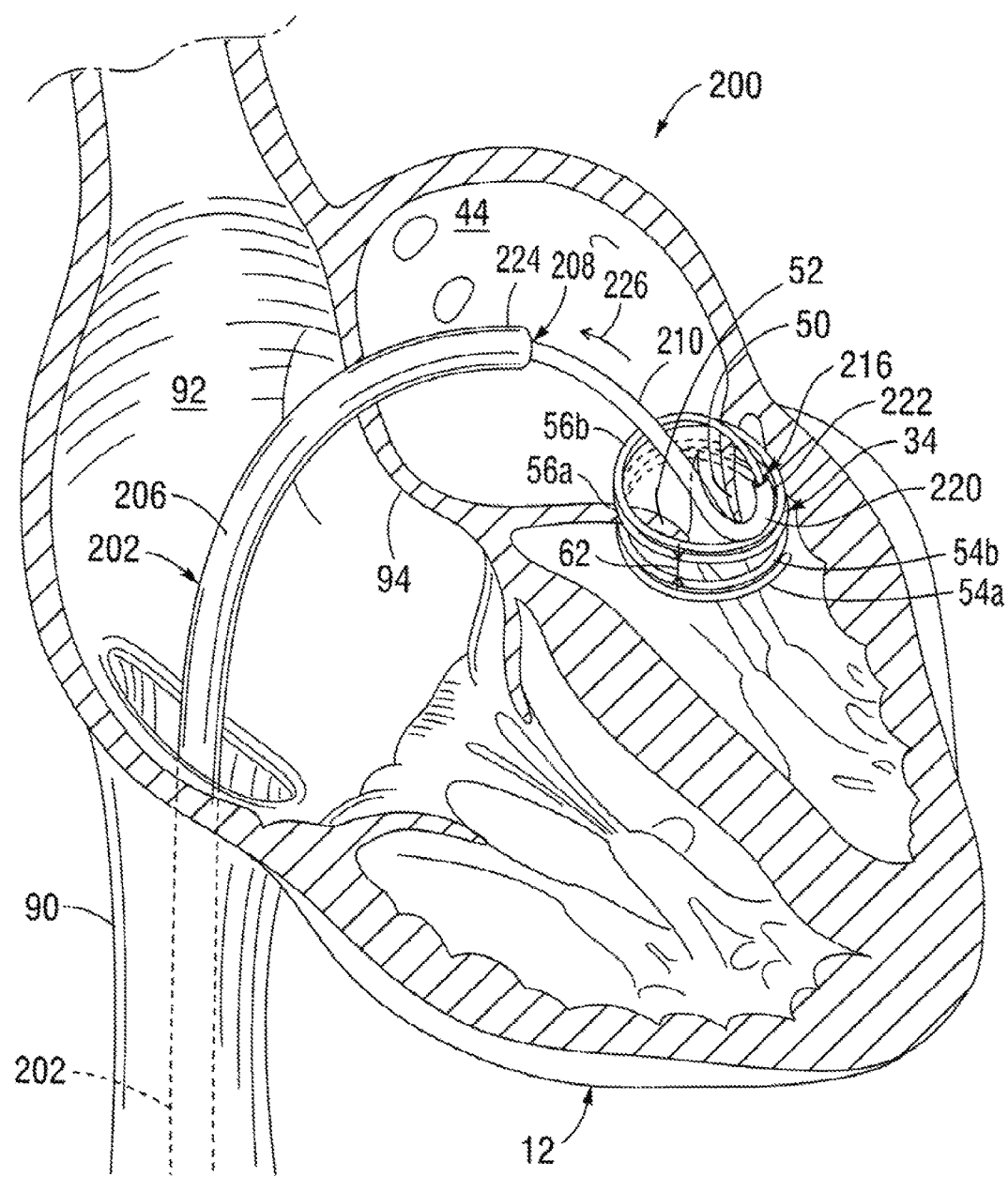

With the ventricular coils 54 of the helical docking device 34 positioned under the leaflets 50, 52, the delivery catheter 204 can then be retracted upwardly in the direction of arrow 226 back into the left atrium 44 (see, e.g., FIG. 5D). Retracting the delivery catheter 204 upwardly in the direction of arrow 226 allows the atrial coils 56a, 56b to be deployed on the atrial side of the mitral valve 42, and also applies a small amount of tension to the docking device as the atrial coils 56a, 56b are deployed to hold the atrial coils slightly spaced above the native leaflets.

The atrial coils 56a, 56b can then be deployed by further advancing the docking device 34 through the lumen 216, for example, by rotating the delivery catheter 204 in the opposite direction of the direction of extension of the coils. FIG. 5D shows the first and the second atrial coils 56a, 56b positioned on the atrial side of the mitral valve 42. The upward tension from the delivery catheter 204 causes the atrial coils 56a, 56b to deploy higher than the ventricular coils 54a, 54b, and creates an axial space 62 and a positive pitch between the second ventricular coil 54b and the first atrial coil 56a, as shown in FIG. 5D.

Figure 5E:
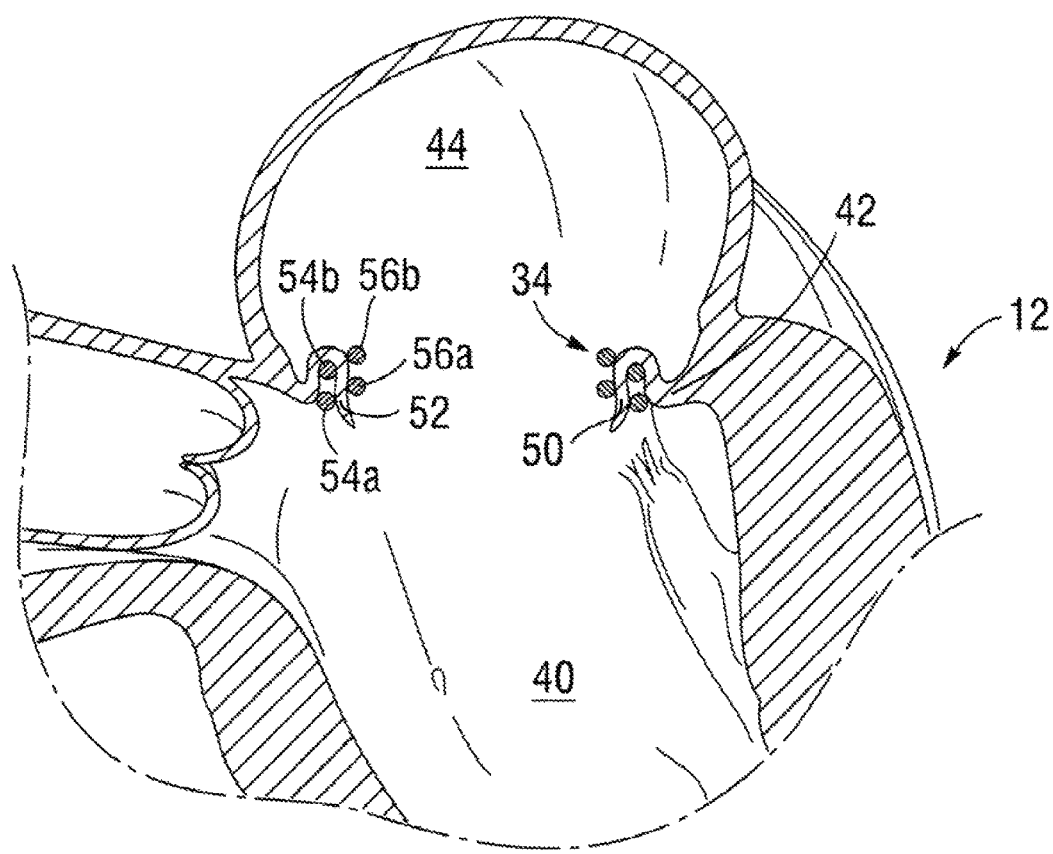

Fully deploying and releasing the docking device 34 from the delivery catheter 204 releases tension on the docking device 34, allowing the atrial coils 56a, 56b to move axially downward towards the ventricular coils 54a, 54b, where the ventricular coils 54a, 54b may also move axially upward towards the atrial coils 56a, 56b, to move the docking device to the axially compressed state, as shown in FIG. 5E. As the atrial coils 56a, 56b nest within the ventricular coils 54a, 54b, the native leaflets 50, 52 become captured between the ventricular coils on the ventricular side of the native leaflets and the atrial coils on the atrial side of the native leaflets.

Once the docking device 34 is secured to the native leaflets 50, 52, the delivery catheter 204 can be removed from the patient's heart 12, for example, by straightening the flexible section 212 and retracting the delivery catheter 204 back through the lumen 208 of the outer catheter 202.

With the delivery catheter 204 removed, a prosthetic valve (e.g., prosthetic valve 36) can then be introduced into the patient's heart 12 using known techniques or methods, for example, as described above with respect to FIGS. 4L-4M. The prosthetic valve can then be secured within the docking device 34, also similarly as described above.

Once the prosthetic valve is secured within the docking device 34, the prosthetic valve delivery apparatus and outer catheter 202 can be removed from the patient's body, and the opening in the patient's septum 94 and right femoral vein can be closed.

FIGS. 6A-6D show a docking device 80, according to a second embodiment. The docking device 80 includes three ventricular coils 82a, 82b, 82c and three atrial coils 84a, 84b, 84c. As can be seen, the atrial coils 84a, 84b, 84c have an inner diameter that is greater than the inner diameter of the ventricular coils 82a, 82b, 82c.

Figure 6A:
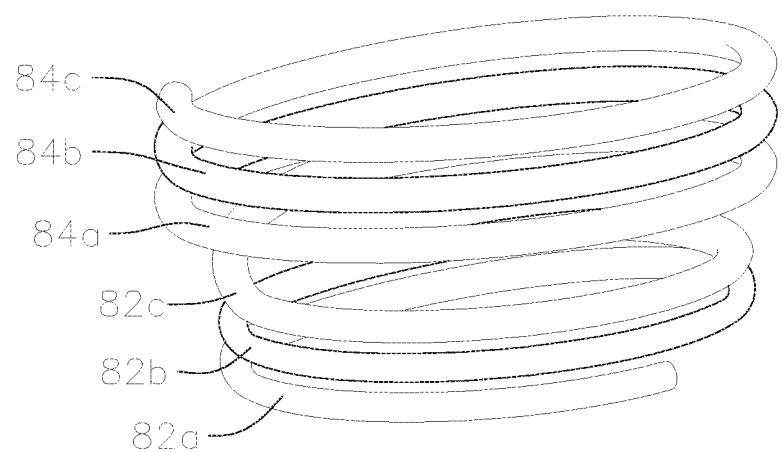
FIG. 6A shows a perspective view of a helical docking device according to a second embodiment of the invention.
Figure 6B:
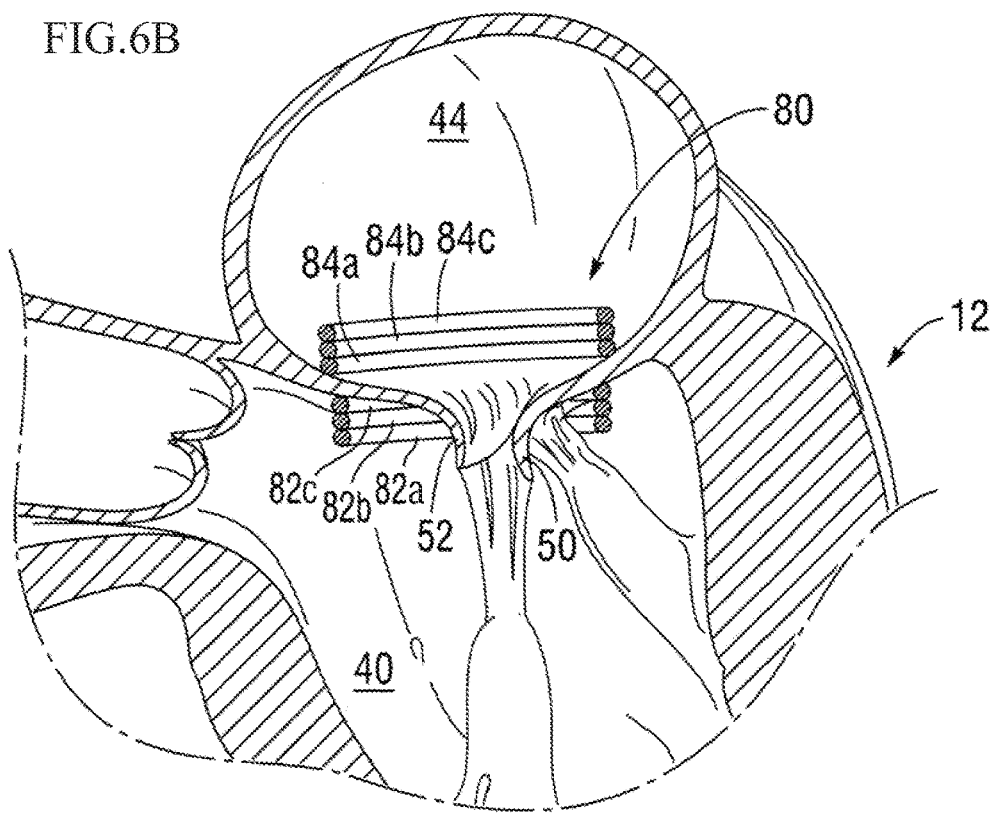
FIGS. 6B-6D show various cross-sectional views of the helical docking device of FIG. 6A implanted at the native mitral valve of a heart.

Like the embodiment of FIGS. 2A-3B, the docking device 80 is axially expandable, for example, when tension is applied to one or both ends of the docking device 80, and is axially compressible, for example, when tension is released from the docking device. FIGS. 6A-6B show the docking device in an axially expanded state, where all the coils extend in a same axial direction and have a positive pitch in this axial direction with respect to adjacent coils.

Figure 6C:
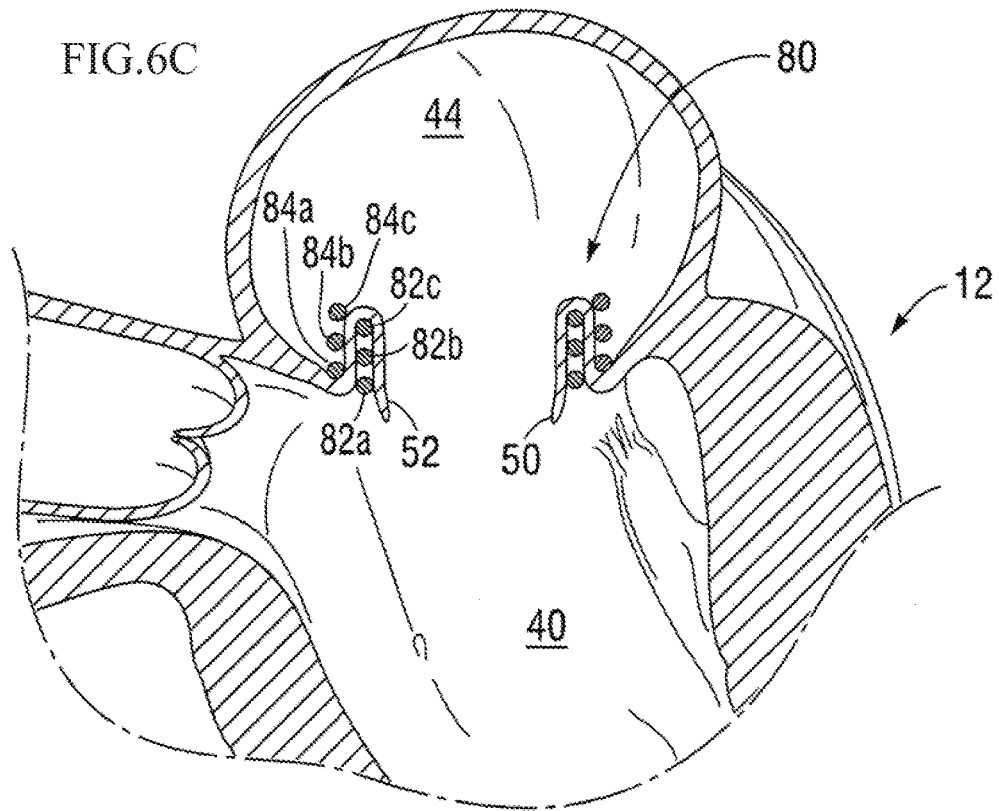
Figure 6D:
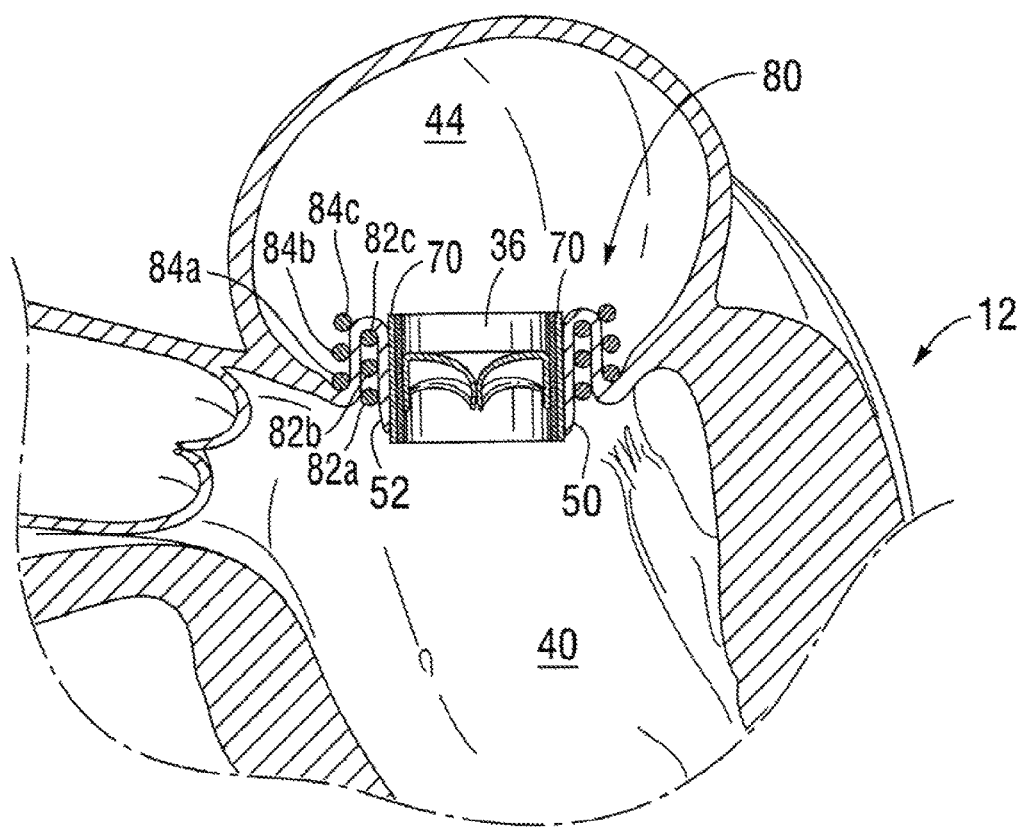

FIGS. 6C-6D show the docking device 80 fully deployed and in an axially compressed state, for example, after tension is released from the docking device 80. In this state, the axial coils and the ventricular coils move towards one another, until at least some of the ventricular coils are nested within the axial coils. In addition, the third ventricular coil 82c is positioned upstream of the first atrial coil 84a, and can therefore be considered to have a negative pitch with respect to the first atrial coil 84a.

By virtue of the docking device 80 assuming the axially compressed state shown in FIGS. 6C-6D, the native mitral valve leaflets 50, 52 become captured and pinched between the atrial coils 84a, 84b, 84c and the ventricular coils 82a, 82b, 82c.

FIG. 6D shows a final configuration where a prosthetic valve 36 is secured in the docking device 80. In some embodiments, a portion of the native leaflets 50, 52 is pinched or otherwise held between the inner coils (the ventricular coils 82a, 82b, 82c in the illustrated embodiment) and the sealing member 70 of the prosthetic valve 36, thereby enhancing the seal between the docking device 34 and the prosthetic valve 36.

Figure 7A:
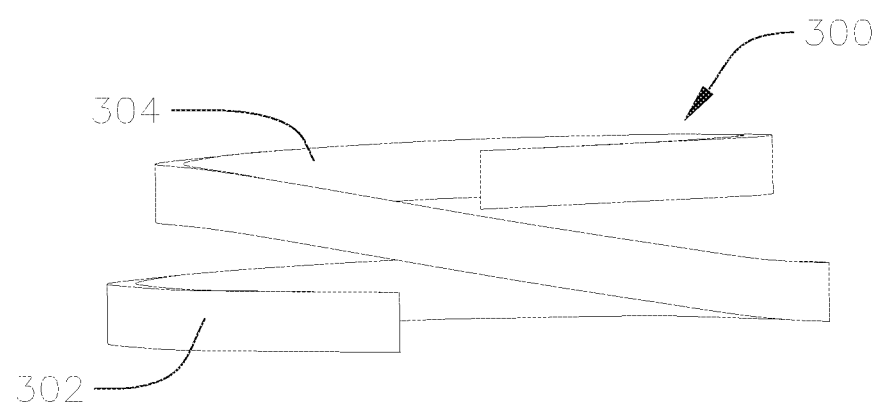
FIG. 7A shows a perspective view of an expanded state of a helical docking device according to a third embodiment of the invention.
Figure 7B:
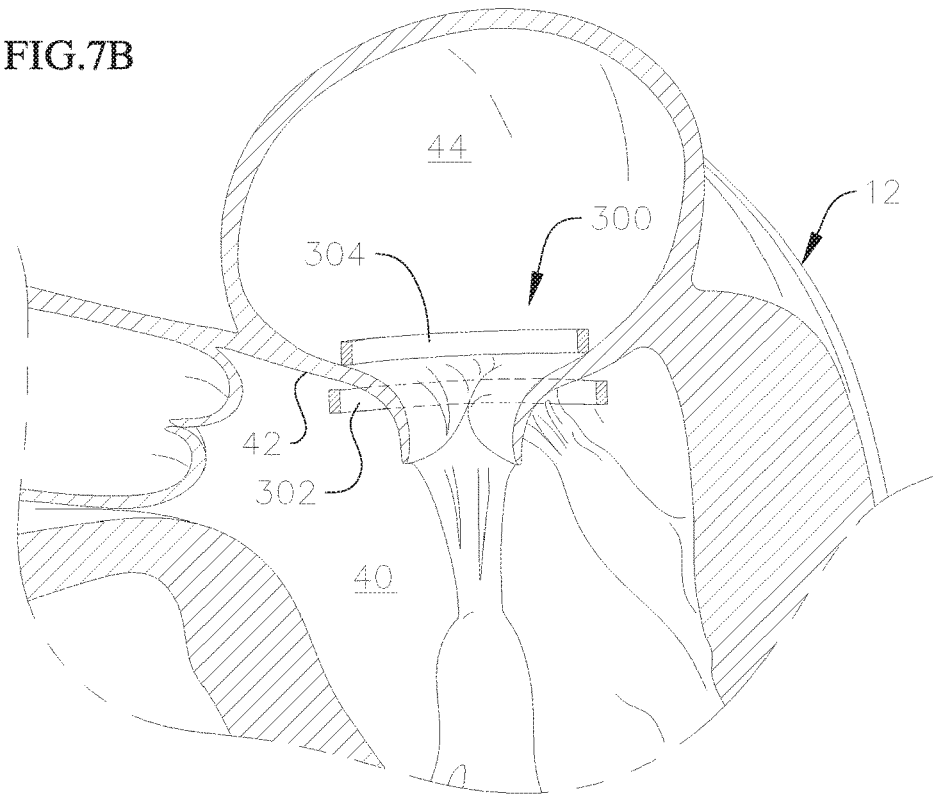
FIGS. 7B and 7C show cross-sectional views of the helical docking device of FIG. 7A at the native mitral valve of a heart.
Figure 7C:
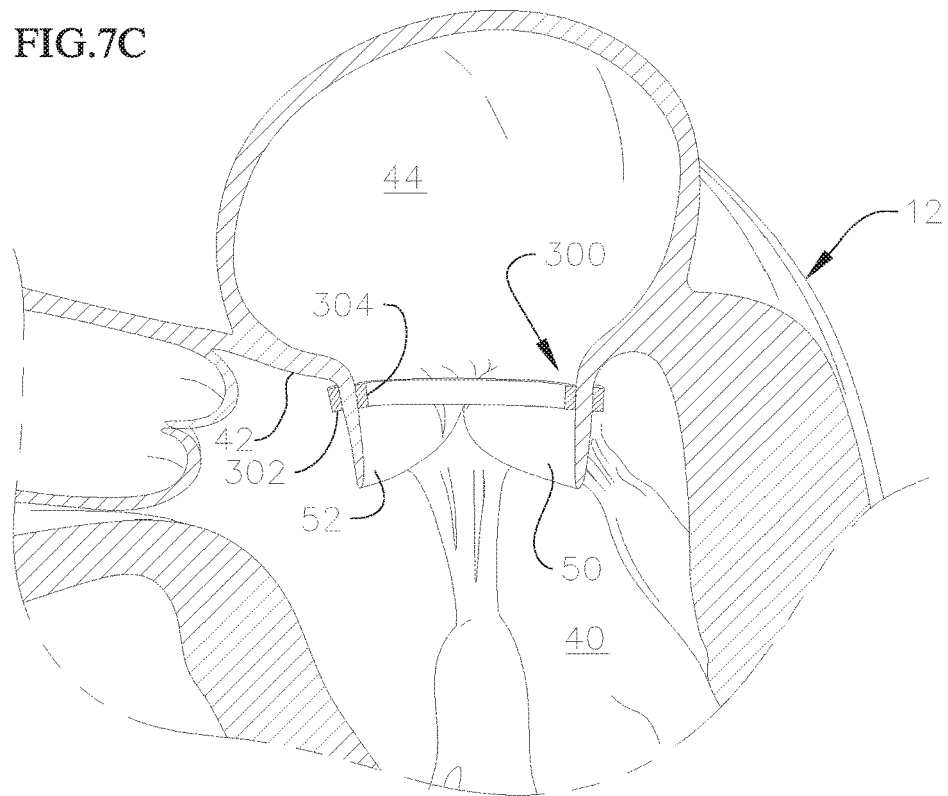

FIGS. 7A-7C show a docking device 300 according to a third embodiment. In the illustrated embodiment, the docking device 300 has one ventricular coil 302 and one atrial coil 304. Similar to the embodiment of FIGS. 2A-3B, the inner diameter of the atrial coil 304 is less than the inner diameter of the ventricular coil 302, allowing the atrial coil 304 to nest with the ventricular coil 302 in the compressed state, similarly as described above with respect to other embodiments. However, unlike the first and second embodiments, the docking device 300 is made of a flat strip of material having a rectangular cross-section. Having a docking device with only one ventricular coil and one atrial coil can, for example, leave more of the native leaflets 50, 52 free (i.e., uncaptured by the docking device 300) in the compressed state, as best shown in FIG. 7C, which for example, can in turn advantageously improve the native leaflets' ability to perform their ordinary function (i.e., opening and closing of the valve during the diastolic and systolic phases of heart contraction, respectively) during the implantation procedure and after the docking device 300 is deployed. Providing a single ventricular coil and a single atrial coil can also, for example, reduce the complexity of the implantation procedure and allow for a more robust design. As can be seen in FIG. 7C, in the compressed state, when the atrial coil 304 is nested inside the ventricular coil 302, the atrial coil 304 can be arranged to be substantially coplanar with or at approximately a same axial position as the ventricular coil 302, such that rather than assuming a negative pitch, the coils in this embodiment can be viewed as being arranged with a zero pitch.

Figure 8A:
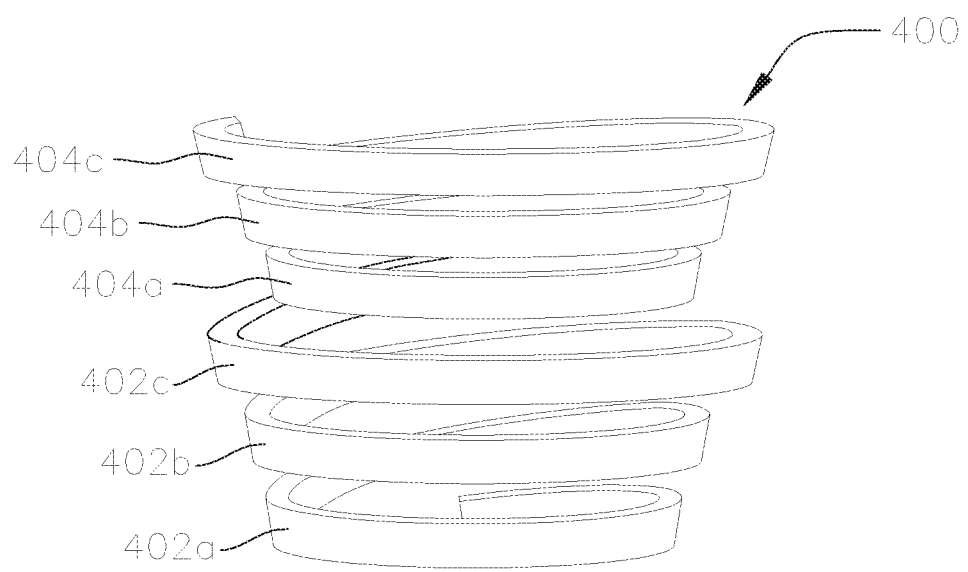
FIG. 8A shows a perspective view of an expanded state of a helical docking device according to a fourth embodiment of the invention.
Figure 8B:
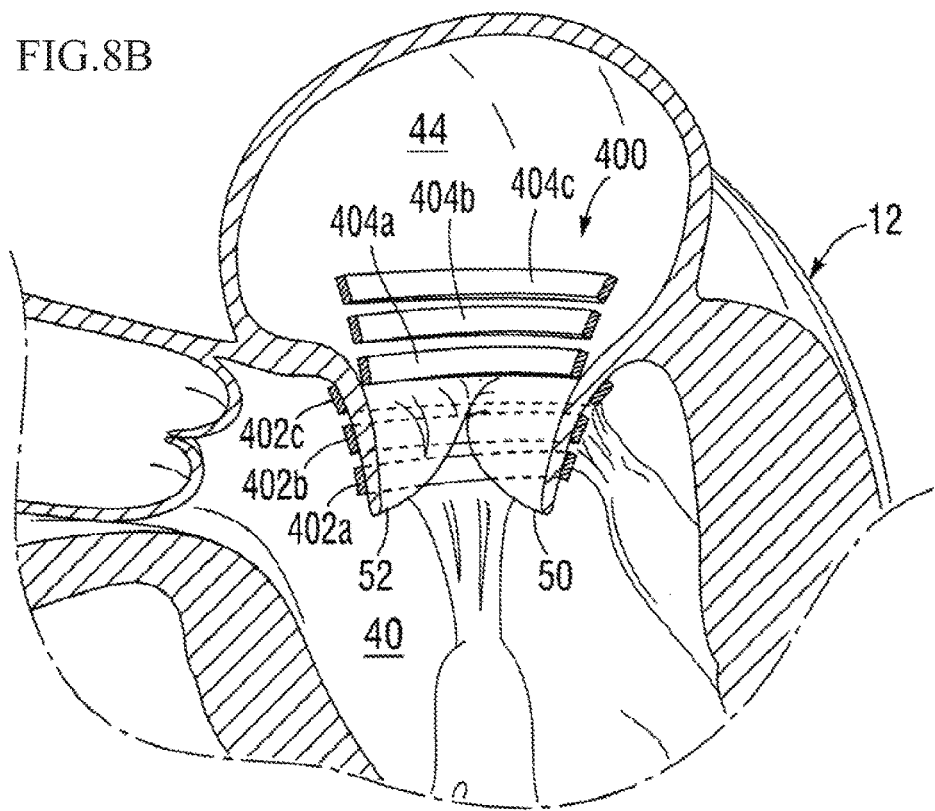
FIGS. 8B and 8C show cross-sectional views of the helical docking device of FIG. 8A at the native mitral valve of a heart.
Figure 8C:
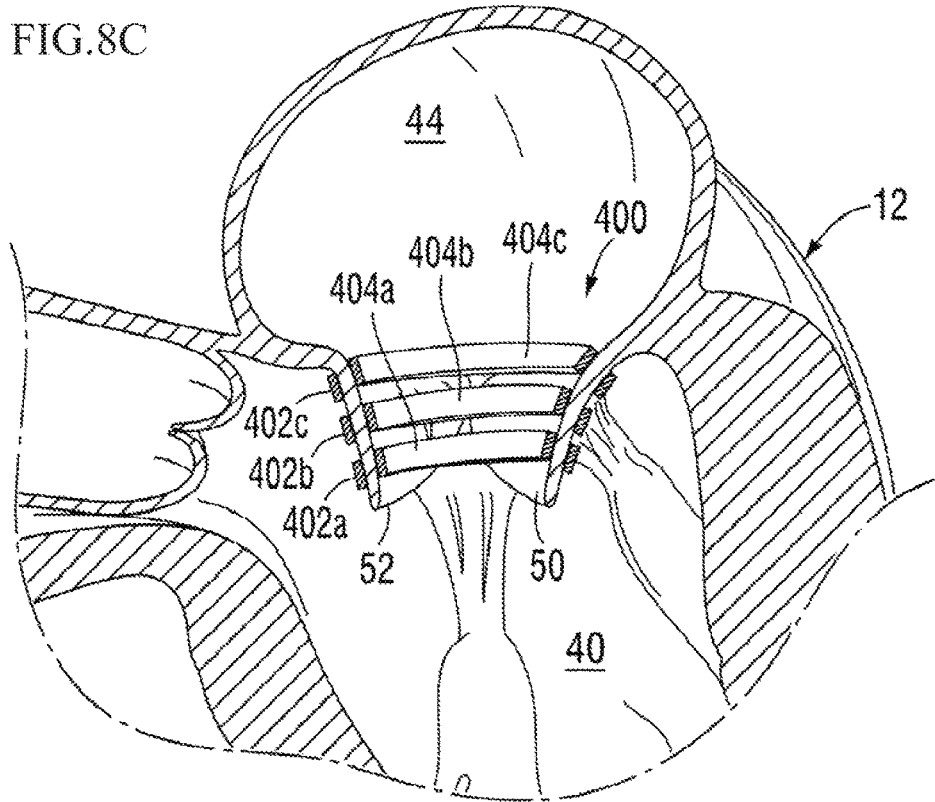

FIGS. 8A-8C show a docking device 400 according to a fourth embodiment. In the illustrated embodiment, the docking device 400 includes three ventricular coils 402a, 402b, 402c and three atrial coils 404a, 404b, 404c. Like the embodiment of FIGS. 7A-7C, the docking device 400 is made of a flat wire having a rectangular cross-section. In addition, the ventricular coil 402a has a smaller inner diameter than the ventricular coil 402b, and the ventricular coil 402b has a smaller inner diameter than the ventricular coil 402c. The atrial coil 404a has a smaller inner diameter than the atrial coil 404b, and the atrial coil 404b has a smaller inner diameter than the atrial coil 404c. In this manner, the atrial coils 404a, 404b, 404c collectively have a conical shape tapering from the uppermost atrial coil 404c to the lowermost atrial coil 404a, and the ventricular coils also collectively have a conical shape tapering from the uppermost ventricular coil 402c to the lowermost ventricular coil 402a.

As best shown in FIG. 8B, the ventricular coil 402a and the atrial coil 404a have substantially similar inner diameters, the ventricular coil 402b and the atrial coil 404b have substantially similar inner diameters, and the ventricular coil 402c and the atrial coil 404c have substantially similar inner diameters. As such, when the device 400 moves from the axially expanded state as shown in FIGS. 8A-8B to the axially compressed state as shown in FIG. 8C, the respective ventricular coils 402a, 402b, 402c can at least partially radially overlap with the atrial coils 404a, 404b, 404c, in a manner similar to a cone within a cone.

Due to the conical shape of the coils, the ventricular coils 402a, 402b, 402c and atrial coils 404a, 404b, 404c can axially interlock in a wedge-like manner with the native leaflets 50, 52 captured between the ventricular coils 402a, 402b, 402c and the atrial coils 404a, 404b, 404c, as shown in FIG. 8C. This wedge-like interlocking can, for example, enhance the retention force applied by the docking device 400 to the native leaflets 50, 52. The conical shape can also, for example, allow the device 400 to better track the natural curved-shape of the native leaflets 50,52. As such, the docking device 400 can be less traumatic to the native leaflet tissue. In addition, the conical shape can, for example, enable better self-alignment of the ventricular coils and the atrial coils as the coils move from the axially expanded state to the axially compressed state.

Figure 9C:
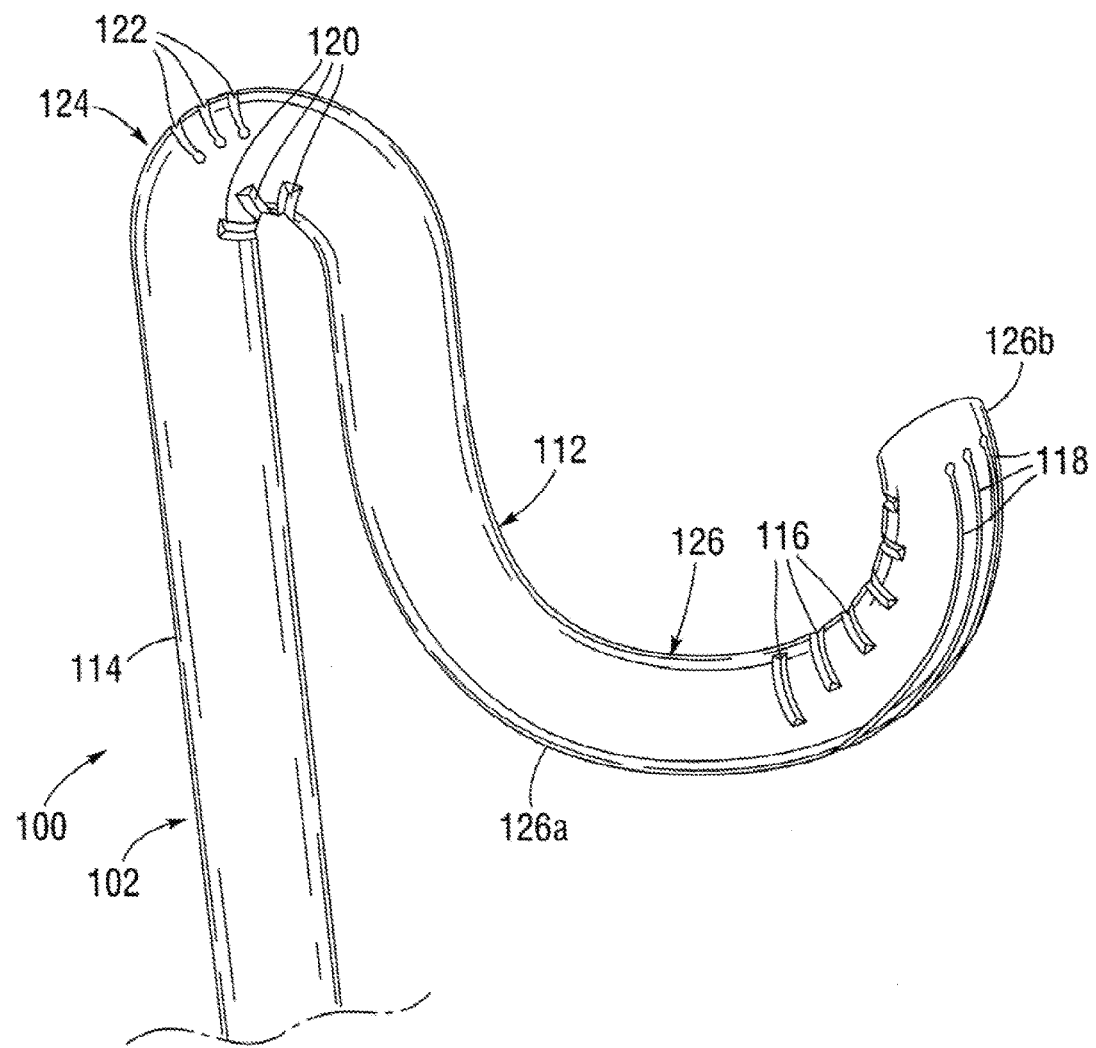

FIGS. 9A-9C show an embodiment of a portion of a delivery catheter 100, similar to guide catheter 16 discussed above, configured for delivering a docking device. The delivery catheter 100 in the illustrated embodiment includes an elongate shaft 102 and a pull wire 104. The shaft 102 has a centrally disposed and axially extending lumen 106, and the pull wire 104 extends co-axially through the lumen 106 of the shaft 102. The distal end 108 of the pull wire 104 can be fixedly secured or attached (e.g., with an adhesive, welding, etc.) to the distal end 110 of the shaft 102. The shaft 102 of the guide catheter 100 has different axial sections, including a flexible, distal section 112 and a relatively more rigid section 114 (e.g., as seen in FIG. 9C) located adjacent and proximal to the flexible, distal section 112.

As shown in FIGS. 9A-9B, near the distal end 110 of the shaft 102, the flexible section 112 has a first plurality of circumferentially extending, axially spaced slots 116 on one side of the shaft and a plurality of diagonally or generally helically extending slots 118 on an opposing side of the shaft. The circumferential slots 116 can be axially spaced apart and angularly offset from each other, such that the slots are spaced relative to each other in a spiral or helical configuration, as best shown in FIG. 9A. The diagonal slots 118 can extend axially and circumferentially in a helical shape, as best shown in FIG. 9B. The circumferential slots 116 are generally diametrically opposed to the diagonal slots 118 on the shaft 102.

The flexible section 112 of the shaft 102 also has a second plurality of circumferential slots 120 and a third plurality of circumferential slots 122, which are positioned proximally relative to the first plurality of circumferential slots 116 and the diagonal slots 118. The second plurality of circumferential slots 120 are axially spaced apart and angularly aligned with each other, as best shown in FIG. 9A. The third plurality of circumferential slots 122 are also axially spaced apart and angularly aligned with each other, as best shown in FIG. 9B. The slots 120 and the slots 122 can also be formed in diametrically opposed sides of the shaft 102 relative to one another.

The shaft 102 can be formed, for example, from a tube. The slots 116, 118, 120, 122 can be formed, for example, by laser cutting the tube. In particular embodiments, the shaft 102 can be formed from an elastically deformable, shape-memory material such as Nitinol.

Due to the manner in which the slots 116, 118, 120, 122 are positioned relative to each other and the widths of the slots, pulling on the proximal end of the pull wire 104 causes the flexible section 112 of the shaft 102 to deform into an activated configuration, as shown in FIG. 9C. Releasing tension on the pull wire 104 allows the flexible section to return to its undeformed, straight configuration.

FIG. 9C shows the activated configuration, in which the flexible section 112 of the shaft 102 forms a first, "U"-shaped curved section 124 and a second, helically curved section 126. The slots 120 are positioned along the inner radius of the curved section 124 and the slots 122 are positioned along the outer radius of the curved section 124. The slots 116 are positioned along the inner radius of the curved section 126 and the slots 118 are positioned along the outer radius of the curved section 126. In the illustrated embodiment, the first curved section 124 forms a 180-degree bend at the end of the rigid section 114 and has a distal section that extends substantially parallel to the rigid section 114. The second curved section 126 has a proximal section 126a that curves radially away from the first curved section 124 in a plane that is substantially perpendicular to the first curved section 124 and a distal tip portion 126b that is angled downwardly away from the plane of the proximal section 126a. The shape of the curved sections 124, 126 can help position a helical docking device relative to the native leaflets 50, 52 when the docking device is deployed from the lumen 106 of the shaft 102, for example, similarly as described above with respect to the delivery catheter 16.

The slots 118, 122 facilitate bending by reducing the strain on the outer radius of the curved sections 124, 126. The slots 116, 118, 120, 122 can also help avoid kinking of the shaft 102, thereby allowing devices (e.g., a docking device 34) to pass more easily through the lumen 106 of the shaft when the flexible section 112 is in the activated configuration.

Although not shown, the guide catheter 100 can have multiple radial layers. For example, the shaft 102 of the guide catheter 100 can have a polymeric outer cover (e.g., PTFE). The guide catheter 100 can also include an alloy or metal mesh or weave (e.g., braided Nitinol). In addition, the interior of the guide catheter can be lined with a lubricious material (e.g., PTFE) to allow other devices and components to pass more easily through the lumen 106 of the shaft 102.

It should be noted that the devices and apparatuses described herein can be used with other placement techniques (e.g., transatrial, open heart, etc.). It should also be noted that the devices described herein (e.g., the helical docking devices and prosthetic valves) can be used in combination with other delivery systems and methods. For example, additional information regarding devices, delivery systems, and methods can be found in U.S. Provisional Patent Application No. 62/088,449 and International Patent Application No. PCT/IB2013/000593 (WIPO Publication No. 2013/114214), which are incorporated by reference herein in their entirety.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language. For example, operations described sequentially can in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms can vary depending on the particular implementation and are readily discernible by one of ordinary skill in the art.

In view of the many possible embodiments to which the principles of the disclosure can be applied, it should be recognized that the illustrated embodiments are only preferred examples of the invention and should not be taken as limiting the scope of the disclosure. Rather, the scope of the disclosure is defined by the following claims.

The invention claimed is:

1. A system for securing a prosthetic heart valve at a native heart valve of a heart of a patient, the system comprising:
    a docking device comprising a first set of one or more coils and a second set of one or more coils, and a central axis extending through the first set of one or more coils and the second set of one or more coils; and
    a prosthetic heart valve configured to be held in the docking device;
    wherein the docking device is configured to assume an axially expanded state wherein the entire first set of one or more coils is positioned on a first side of the second set of one or more coils relative to the central axis; and
    wherein the docking device is configured to assume an axially compressed state wherein a first coil of the first set of one or more coils is positioned on a second side of at least a portion of the second set of one or more coils opposite to the first side relative to the central axis.

2. The system of claim 1, further comprising a delivery catheter, wherein the delivery catheter is configured to deploy the docking device at the native heart valve.

3. The system of claim 1, wherein the first set of one or more coils has a first inner diameter, and the second set of one or more coils has a second inner diameter different from the first inner diameter.

4. The system of claim 1, wherein the first set of one or more coils comprises at least two coils and the second set of one or more coils comprises at least two coils.

5. The system of claim 4, wherein at least one of the coils of the first set of one or more coils is positioned relative to the central axis between two coils of the second set of one or more coils when the docking device is in the compressed state.

6. The system of claim 1, wherein the first set of one or more coils is configured to be positioned on a ventricular side of a native mitral valve, and the second set of one or more coils is configured to be positioned on an atrial side of the native mitral valve.

7. The system of claim 1, wherein the first set of one or more coils and the second set of one or more coils each comprises a shape-memory material.

8. The system of claim 1, wherein the first set of one or more coils is positioned radially inward relative to the second set of one or more coils when the docking device is in the compressed state.

9. The system of claim 8, wherein the first set of one or more coils is configured to exert a radially outwardly directed force against the second set of one or more coils when the device is in the compressed state.

10. The system of claim 1, wherein, when in the axially expanded state, the entire first set of one or more coils and the entire second set of one or more coils have a positive pitch relative to each other, and when in the axially compressed state, at least a portion of the first set of one or more coils has a negative pitch relative to the second set of one or more coils.

11. A method of using the system of claim 1 to treat a native valve of a heart of a patient, the method comprising:
positioning the first set of one or more coils on a first side of the native valve;
positioning the second set of one or more coils on a second side of the native valve, such that the entire first set of one or more coils is positioned on a first side of the second set of one or more coils relative to a central axis of the device; and
transitioning the docking device to a position where the first coil of the first set of one or more coils is positioned on a second side of at least a portion of the second set of one or more coils opposite to the first side relative to the central axis.

12. The method of claim 11, further comprising implanting the prosthetic heart valve in the device.

13. The method of claim 12, wherein implanting the prosthetic heart valve comprises positioning the prosthetic heart valve in the device when the prosthetic heart valve is in a radially compressed state, and radially expanding the prosthetic heart valve such that a radial pressure is applied between the prosthetic heart valve and the device to anchor the prosthetic heart valve in the device.

14. The method of claim 11, wherein after transitioning the device, the first coil is configured to be positioned between two coils of the second set of coils relative to the central axis.

15. The method of claim 11, wherein the first set of one or more coils and the second set of one or more coils of the device are configured to radially compress leaflets of the native valve.

16. The method of claim 11, wherein positioning the first set of one or more coils comprises advancing a distal end of a delivery catheter into the heart, and deploying the first set of one or more coils from the delivery catheter on the atrial side of the native valve, and wherein positioning the second set of one or more coils comprises deploying the second set of one or more coils on the ventricular side of the native valve.

17. The method of claim 16, wherein positioning the first set of one or more coils further comprises maintaining an axial tension on the docking device when the docking device is being deployed from the delivery catheter, such that the docking device is at least partially axially expanded, and wherein transitioning the docking device comprises releasing tension on the docking device to allow the device to compress axially.

* * * * *